United States Patent
Mischler et al.

(10) Patent No.: US 11,931,585 B2
(45) Date of Patent: Mar. 19, 2024

(54) METHOD AND APPARATUS FOR DETECTING CARDIAC EVENT OVERSENSING

(71) Applicant: Medtronic, Inc., Minneapolis, MN (US)

(72) Inventors: Gavin M. Mischler, Wilmette, IL (US); Yuanzhen Liu, Minneapolis, MN (US); Saul E. Greenhut, Denver, CO (US); Xusheng Zhang, Shoreview, MN (US)

(73) Assignee: Medtronic, Inc., Minneapolis, MN (US)

(*) Notice: Subject to any disclaimer, the term of this patent is extended or adjusted under 35 U.S.C. 154(b) by 450 days.

(21) Appl. No.: 17/109,968

(22) Filed: Dec. 2, 2020

(65) Prior Publication Data

US 2021/0170170 A1 Jun. 10, 2021

Related U.S. Application Data

(60) Provisional application No. 62/945,430, filed on Dec. 9, 2019.

(51) Int. Cl.
| | |
|---|---|
| A61N 1/362 | (2006.01) |
| A61B 5/352 | (2021.01) |
| A61B 5/363 | (2021.01) |
| A61N 1/365 | (2006.01) |
| A61N 1/37 | (2006.01) |

(52) U.S. Cl.
CPC .......... *A61N 1/3621* (2013.01); *A61B 5/352* (2021.01); *A61B 5/363* (2021.01); *A61N 1/365* (2013.01); *A61N 1/3704* (2013.01); *A61N 1/3706* (2013.01)

(58) Field of Classification Search
CPC .......... A61B 5/316; A61B 5/349; A61B 5/35; A61B 5/363; A61B 5/7221
See application file for complete search history.

(56) References Cited

U.S. PATENT DOCUMENTS

| | | |
|---|---|---|
| 5,893,882 A | 4/1999 | Peterson et al. |
| 7,031,771 B2 | 4/2006 | Brown et al. |
| 7,130,677 B2 | 10/2006 | Brown et al. |
| 7,283,863 B2 | 10/2007 | Gunderson et al. |
| 7,496,403 B2 | 2/2009 | Cao et al. |
| 7,496,409 B2 | 2/2009 | Greenhut et al. |
| 7,734,333 B2 | 6/2010 | Ghanem et al. |
| 7,734,336 B2 | 6/2010 | Ghanem et al. |
| 7,742,812 B2 | 6/2010 | Ghanem et al. |

(Continued)

OTHER PUBLICATIONS

PCT International Written Opinion of International Searching Authority Completed Mar. 3, 2021, corresponding to counterpart, PCT International Patent Application No. PCT/US2020/063188, 5 pages.

(Continued)

*Primary Examiner* — Allen Porter

(57) ABSTRACT

A medical device is configured to detect an alternating pattern of signal features determined from consecutive segments of a cardiac electrical signal and determine a gross morphology metric from at least one segment of the cardiac electrical signal. The device is configured to detect cardiac event oversensing in response to detecting the alternating pattern and the gross morphology metric not meeting tachyarrhythmia morphology criteria. The medical device may withhold detecting an arrhythmia in response to detecting the cardiac event oversensing.

29 Claims, 11 Drawing Sheets

(56) References Cited

U.S. PATENT DOCUMENTS

| | | |
|---|---|---|
| 7,761,142 B2 | 7/2010 | Ghanem et al. |
| 7,761,150 B2 | 7/2010 | Ghanem et al. |
| 7,769,452 B2 | 8/2010 | Ghanem et al. |
| 7,774,049 B2 | 8/2010 | Ghanem et al. |
| 7,783,354 B2 | 8/2010 | Gunderson |
| 7,813,791 B1 | 10/2010 | Gill et al. |
| 7,826,893 B2 | 11/2010 | Cao et al. |
| 7,894,894 B2 | 2/2011 | Stadler et al. |
| 7,904,153 B2 | 3/2011 | Greenhut et al. |
| 7,907,993 B2 | 3/2011 | Ghanem et al. |
| 7,937,135 B2 | 5/2011 | Ghanem et al. |
| 7,941,214 B2 | 5/2011 | Kleckner et al. |
| 7,991,471 B2 | 8/2011 | Ghanem et al. |
| 8,050,751 B2 | 11/2011 | Zhang et al. |
| 8,050,759 B2 | 11/2011 | Stegemann et al. |
| 8,068,901 B2 | 11/2011 | Ghanem et al. |
| 8,095,205 B2 | 1/2012 | Bhunia |
| 8,095,206 B2 | 1/2012 | Ghanem et al. |
| 8,145,307 B2 | 3/2012 | Zhang et al. |
| 8,160,684 B2 | 4/2012 | Ghanem et al. |
| 8,160,686 B2 | 4/2012 | Allavatam et al. |
| 8,170,654 B1 | 5/2012 | Zhang et al. |
| 8,271,073 B2 | 9/2012 | Zhang et al. |
| 8,301,233 B2 | 10/2012 | Zhang et al. |
| 8,306,618 B2 | 11/2012 | Ghanem et al. |
| 8,386,024 B2 | 2/2013 | Gunderson et al. |
| 8,435,185 B2 | 5/2013 | Ghanem et al. |
| 8,521,275 B2 | 8/2013 | Stadler et al. |
| 8,577,455 B2 | 11/2013 | Mitrani et al. |
| 8,781,585 B2 | 7/2014 | Gunderson et al. |
| 8,792,971 B2 | 7/2014 | Gunderson et al. |
| 8,855,755 B2 | 10/2014 | Zhang et al. |
| 9,022,962 B2 | 5/2015 | Brown |
| 9,174,062 B2 | 11/2015 | Stadler et al. |
| 9,375,181 B2 | 6/2016 | Hemming et al. |
| 9,526,908 B2 | 12/2016 | Zhang et al. |
| 9,561,005 B2 | 2/2017 | Zhang |
| 9,566,012 B2 | 2/2017 | Greenhut et al. |
| 9,586,051 B2 | 3/2017 | Greenhut et al. |
| 9,597,525 B2 | 3/2017 | Cao et al. |
| 9,872,630 B2 | 1/2018 | Stadler et al. |
| 9,956,423 B2 | 5/2018 | Zhang et al. |
| 10,130,818 B2 | 11/2018 | Greenhut et al. |
| 10,188,867 B2 | 1/2019 | Zhang |
| 10,252,071 B2 | 4/2019 | Cao et al. |
| 10,265,536 B2 | 4/2019 | Stadler et al. |
| 10,328,274 B2 | 6/2019 | Zhang et al. |
| 10,376,705 B2 | 8/2019 | Zhang et al. |
| 10,406,373 B2 | 9/2019 | Zhang |
| 10,470,681 B2 | 11/2019 | Greenhut et al. |
| 10,493,291 B2 | 12/2019 | Cao et al. |
| 10,507,332 B2 | 12/2019 | Zhang et al. |
| 10,555,684 B2 | 2/2020 | Zhang et al. |
| 10,561,332 B2 | 2/2020 | Zhang et al. |
| 10,576,288 B2 | 3/2020 | Cao et al. |
| 10,583,306 B2 | 3/2020 | Zhang et al. |
| 10,799,710 B2 | 10/2020 | Cao et al. |
| 2013/0096445 A1 | 4/2013 | Patel |
| 2016/0158567 A1 | 6/2016 | Marshall et al. |
| 2017/0043173 A1 | 2/2017 | Sharma et al. |
| 2018/0028083 A1 | 2/2018 | Greenhut et al. |
| 2018/0028085 A1 | 2/2018 | Zhang et al. |
| 2018/0028828 A1 | 2/2018 | Cao et al. |
| 2018/0303368 A1 | 10/2018 | Zhang et al. |
| 2019/0111268 A1 | 4/2019 | Christie et al. |
| 2019/0184164 A1 | 6/2019 | Zhang et al. |
| 2019/0308026 A1 | 10/2019 | Zhang et al. |
| 2019/0314637 A1 | 10/2019 | Stadler et al. |
| 2019/0374783 A1 | 12/2019 | Zhang et al. |
| 2020/0046988 A1 | 2/2020 | Wilkinson et al. |
| 2020/0094065 A1 | 3/2020 | Cao et al. |
| 2020/0114158 A1 | 4/2020 | Zhang et al. |
| 2020/0170532 A1 | 6/2020 | Zhang et al. |
| 2020/0178830 A1 | 6/2020 | Zhang et al. |
| 2020/0197708 A1 | 6/2020 | Cao et al. |

OTHER PUBLICATIONS

PCT International Search Report Completed Mar. 3, 2021, corresponding to counterpart, PCT International Patent Application No. PCT/US2020/063188, 3 pages.

METHOD AND APPARATUS FOR DETECTING CARDIAC EVENT OVERSENSING

CROSS-REFERENCE TO RELATED APPLICATIONS

This application claims the benefit of and priority to U.S. Provisional Patent Application Ser. No. 62/945,430 filed Dec. 9, 2019, the entire disclosure of which is incorporated by reference herein.

TECHNICAL FIELD

The disclosure relates generally to a medical device system and method for detecting oversensing of cardiac events in a cardiac electrical signal.

BACKGROUND

Medical devices, such as cardiac pacemakers and implantable cardioverter defibrillators (ICDs), provide therapeutic electrical stimulation to a heart of a patient via electrodes carried by one or more medical electrical leads and/or electrodes on a housing of the medical device. The electrical stimulation may include signals such as pacing pulses or cardioversion or defibrillation shocks. In some cases, a medical device may sense cardiac electrical signals attendant to the intrinsic or pacing-evoked depolarizations of the heart and control delivery of stimulation signals to the heart based on sensed cardiac electrical signals. Upon detection of an abnormal rhythm, such as bradycardia, tachycardia or fibrillation, an appropriate electrical stimulation signal or signals may be delivered to restore or maintain a more normal rhythm of the heart. For example, an ICD may deliver pacing pulses to the heart of the patient upon detecting bradycardia or tachycardia or deliver cardioversion or defibrillation (CV/DF) shocks to the heart upon detecting tachycardia or fibrillation.

The ICD may sense the cardiac electrical signals in a heart chamber and deliver electrical stimulation therapies to the heart chamber using electrodes carried by transvenous medical electrical leads. Cardiac signals sensed within a heart chamber generally have a high signal strength and quality for reliably sensing near-field cardiac electrical events, such as ventricular R-waves sensed from within a ventricle, without oversensing of far-field events arising from other heart chambers, such as P-waves. In some proposed or available ICD systems, a non-transvenous lead may be coupled to the ICD, in which case cardiac signal sensing presents new challenges in accurately sensing cardiac electrical events from outside a heart chamber.

SUMMARY

In general, the disclosure is directed to techniques for detecting oversensing of cardiac events from a cardiac electrical signal and rejecting an arrhythmia detection in response to detecting the cardiac event oversensing. In some instances, the oversensed cardiac events may be P-waves that are falsely sensed as R-waves from a cardiac electrical signal. Oversensed P-waves may be counted toward the detection of a ventricular tachyarrhythmia leading to anti-tachyarrhythmia pacing or a CV/DF shock. A medical device, such as a pacemaker or ICD, operating according to the techniques disclosed herein may detect oversensing of P-waves and does not detect a ventricular tachyarrhythmia based on a count of tachyarrhythmia intervals reaching a detection threshold criteria in response to detecting the oversensed P-waves. In this way, a tachyarrhythmia therapy, such as anti-tachycardia pacing and/or CV/DV shock(s), may be withheld when oversensing is detected.

In some examples, the cardiac electrical signal is sensed via an extracardiovascular lead used for sensing the cardiac events, e.g., R-waves, and delivering cardiac electrical stimulation therapies via extracardiovascular electrodes based on sensed cardiac events. A medical device operating according to the techniques disclosed herein may sense cardiac events from a first cardiac electrical signal and detect oversensing of cardiac events from the first cardiac electrical signal by determining features of consecutive time segments of a second cardiac electrical signal. The device may detect cardiac event oversensing based on identifying an alternating pattern of the second cardiac electrical signal features. Cardiac event oversensing detection may include verifying that the consecutive second cardiac electrical signal segments presenting the alternating pattern of signal features do not include a tachyarrhythmia morphology.

In one example, the disclosure provides a medical device including a cardiac electrical signal sensing circuit and a control circuit. The cardiac electrical signal sensing circuit is configured to sense at least one cardiac electrical signal and detect cardiac events from the at least one cardiac electrical signal. The control circuit is configured to determine a signal feature from a segment of the at least one cardiac electrical signal in response to each one of a plurality of cardiac events detected from the at least one cardiac electrical signal, detect an alternating pattern of the signal feature determined from the consecutive segments of the at least one cardiac electrical signal, determine a gross morphology metric from each of at least one segment of the consecutive segments, and detect cardiac event oversensing in response to the gross morphology metric not meeting a tachyarrhythmia morphology criteria and detecting the alternating pattern. The control circuit withholds detection of an arrhythmia in response to detecting the cardiac event oversensing.

In another example, the disclosure provides a method including sensing at least one cardiac electrical signal and detecting cardiac events from the at least one cardiac electrical signal. The method includes determining a signal feature from a segment of the at least one cardiac electrical signal in response to each one of a plurality of cardiac events detected from the at least one cardiac electrical signal, detecting an alternating pattern of the signal feature determined from consecutive segments of the at least one cardiac electrical signal and determining a gross morphology metric from each of at least one segment of the consecutive segments. The method further includes determining that the gross morphology metric does not meet a tachyarrhythmia morphology criteria, detecting cardiac event oversensing in response to the gross morphology metric not meeting the tachyarrhythmia morphology criteria and detecting the alternating pattern, and withholding detection of an arrhythmia in response to detecting the cardiac event oversensing evidence.

In another example, the disclosure provides a non-transitory, computer-readable storage medium storing a set of instructions which, when executed by a control circuit of a medical device, cause the medical device to sense at least one cardiac electrical signal, detect cardiac events from the at least one cardiac electrical signal, and determine a signal feature from a segment of the at least one cardiac electrical signal in response to each one of a plurality of cardiac events detected from the at least one cardiac electrical signal. The medical device is further caused to detect an alternating pattern of the signal features determined from consecutive segments of the at least one cardiac electrical signal, determine a gross morphology metric from each of at least one segment of the consecutive segments, determine that the gross morphology metric does not meet a tachyarrhythmia morphology criteria, and detect cardiac event oversensing in response to the gross morphology metric not meeting the tachyarrhythmia morphology criteria and detecting the alternating pattern. The medical device is caused to withhold detection of an arrhythmia in response to detecting the cardiac event oversensing.

This summary is intended to provide an overview of the subject matter described in this disclosure. It is not intended to provide an exclusive or exhaustive explanation of the apparatus and methods described in detail within the accompanying drawings and description below. Further details of one or more examples are set forth in the accompanying drawings and the description below.

DETAILED DESCRIPTION

Figure 1A:
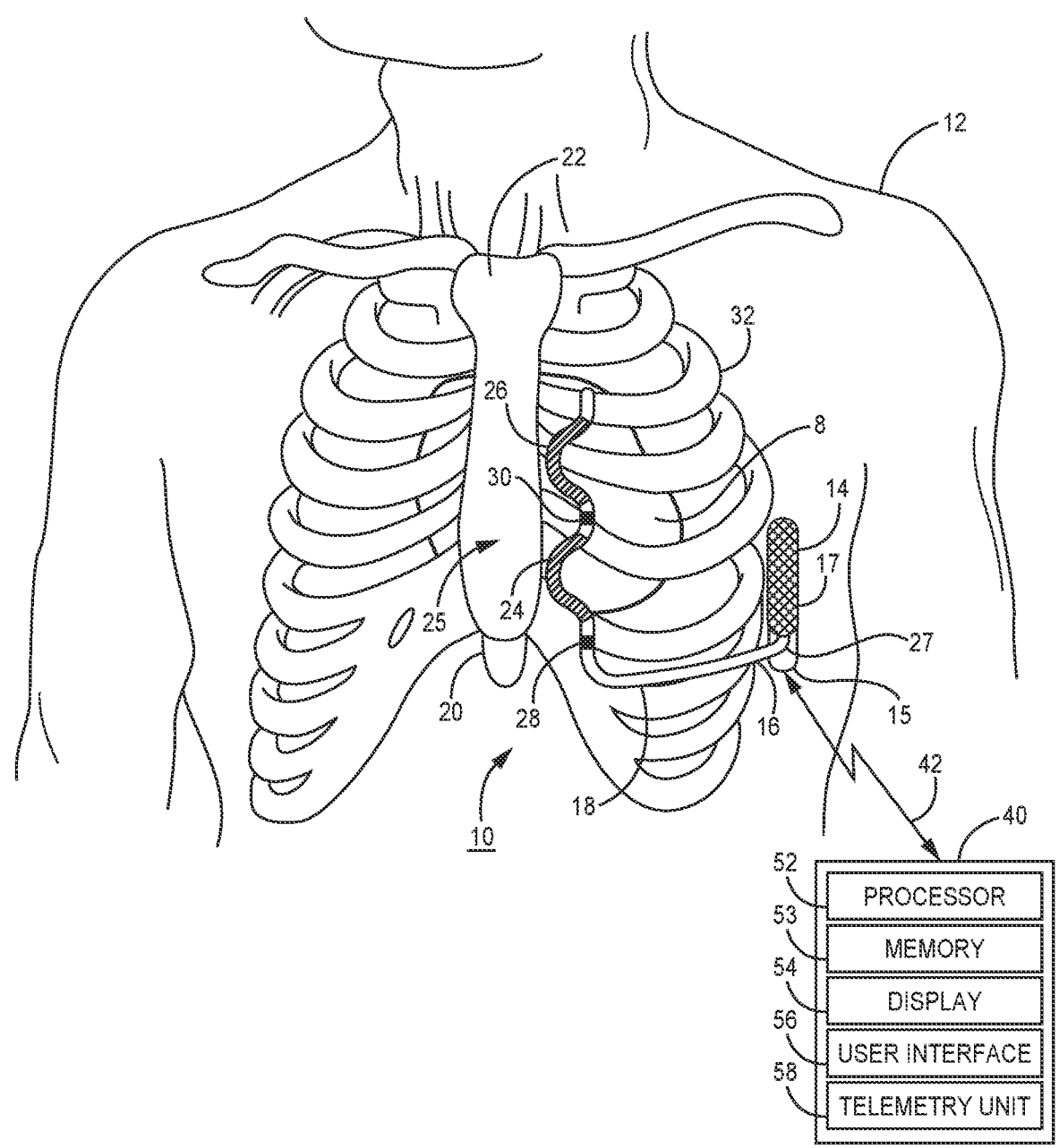
FIGS. 1A and 1B are conceptual diagrams of an extra-cardiovascular ICD system configured to sense cardiac electrical events and deliver cardiac electrical stimulation therapies according to one example.

In general, this disclosure describes techniques for detecting cardiac event oversensing by a medical device or system. In some examples, a medical device may be configured to sense R-waves attendant to ventricular depolarizations for use in controlling ventricular pacing and detecting ventricular tachyarrhythmias. A ventricular tachyarrhythmia may be detected in response to sensing a threshold number of R-waves occurring at time intervals that are less than a tachyarrhythmia detection interval. In some instances, atrial P-waves attendant to atrial depolarizations may be oversensed as R-waves. An oversensed P-wave may cause the medical device to count a ventricular tachyarrhythmia interval when a P-wave is falsely sensed as an R-wave within the tachyarrhythmia interval of a true sensed R-wave, potentially leading to a false ventricular tachyarrhythmia detection and inappropriate CV/DF shock or other therapy delivered by the cardiac medical device, such as anti-tachyarrhythmia pacing (ATP). By identifying oversensing of P-waves, a ventricular tachyarrhythmia detection due to the P-wave oversensing (PWOS) may be rejected. A medical device performing the techniques disclosed herein may detect cardiac event oversensing for the purposes of controlling a tachyarrhythmia therapy.

In some examples, the medical device system performing the techniques disclosed herein may be an extra-cardiovascular ICD system. As used herein, the term "extra-cardiovascular" refers to a position outside the blood vessels, heart, and pericardium surrounding the heart of a patient. Implantable electrodes carried by extra-cardiovascular leads may be positioned extra-thoracically (outside the ribcage and sternum) or intra-thoracically (beneath the ribcage or sternum) but generally not in intimate contact with myocardial tissue. The techniques disclosed herein for detecting P-wave oversensing may be applied to a cardiac electrical signal sensed using extra-cardiovascular electrodes.

The cardiac event oversensing detection techniques are described herein in conjunction with an ICD and an implantable extra-cardiovascular medical lead carrying sensing and therapy delivery electrodes, but aspects disclosed herein may be utilized in conjunction with other cardiac medical devices or systems. For example, the techniques for detecting P-wave oversensing as described in conjunction with the accompanying drawings may be implemented in any implantable or external medical device enabled for sensing intrinsic cardiac electrical events from cardiac signals received from a patient's heart via sensing electrodes, including implantable pacemakers, ICDs or cardiac monitors coupled to transvenous, pericardial or epicardial leads carrying sensing and therapy delivery electrodes; leadless pacemakers, ICDs or cardiac monitors having housing-based sensing electrodes; and external or wearable pacemakers, defibrillators, or cardiac monitors coupled to external, surface or skin electrodes.

Furthermore, while the techniques disclosed herein are described for the detection of oversensing of P-waves as R-waves, the disclosed techniques may be used for detecting oversensing of other cardiac events, e.g., oversensing of R-waves as P-waves potentially leading to false atrial tachyarrhythmia detection. Atrial P-waves may be sensed from a cardiac electrical signal, e.g., received by lead-based electrodes or a leadless pacemaker in the atrium, and oversensing of R-waves as P-waves may be detected.

Figure 1B:
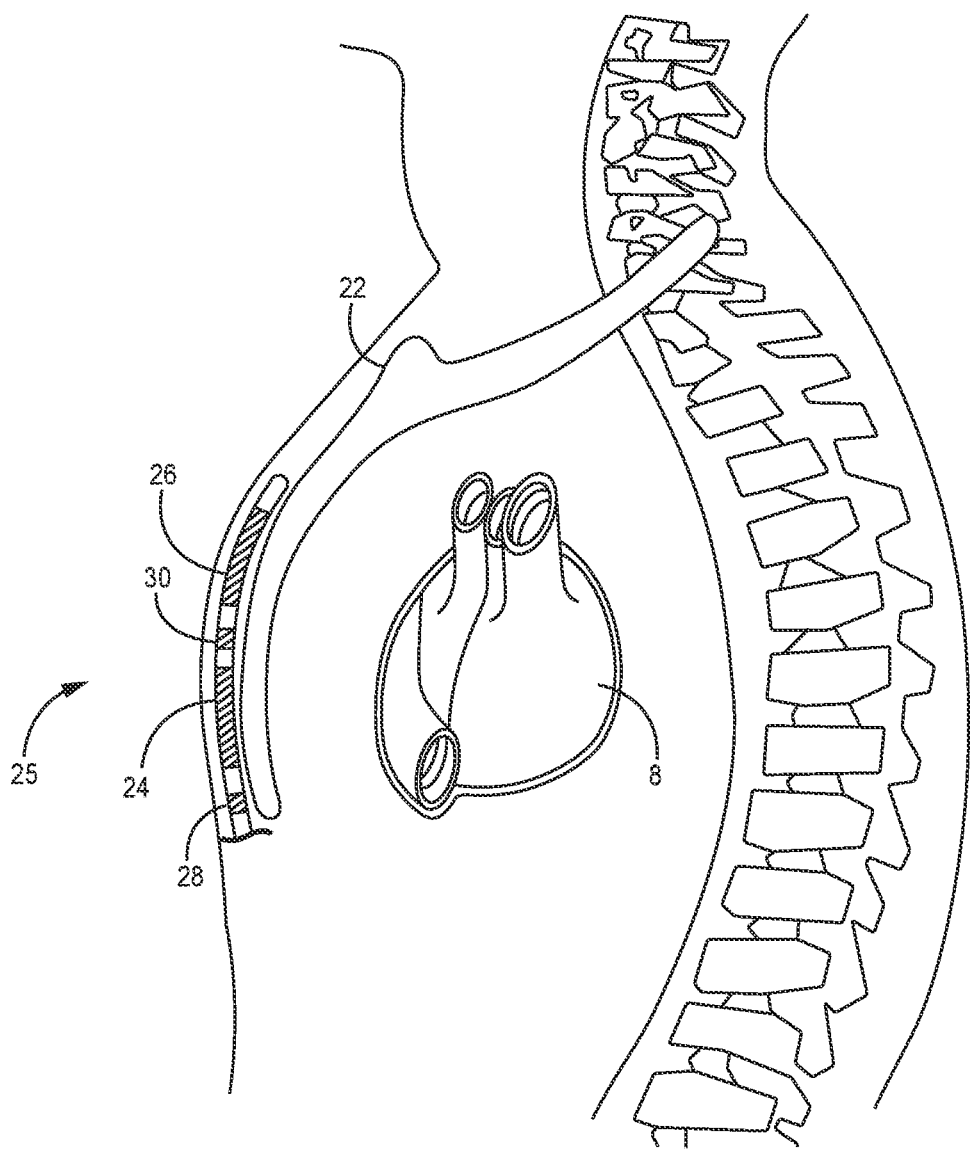

FIGS. 1A and 1B are conceptual diagrams of an extra-cardiovascular ICD system 10 configured to sense cardiac electrical events and deliver cardiac electrical stimulation therapies according to one example. FIG. 1A is a front view of ICD system 10 implanted within patient 12. FIG. 1B is a side view of ICD system 10 implanted within patient 12. ICD system 10 includes an ICD 14 connected to an extra-cardiovascular electrical stimulation and sensing lead 16. FIGS. 1A and 1B are described in the context of an ICD system 10 capable of providing high voltage CV/DF shocks, and in some examples cardiac pacing pulses, in response to detecting a cardiac tachyarrhythmia. However, the techniques disclosed herein for detecting cardiac event oversensing may be implemented in other cardiac devices configured for sensing cardiac events and, for example, determining a cardiac event interval or rate, for use in determining the cardiac rate or rhythm and controlling a cardiac electrical stimulation therapy.

ICD 14 includes a housing 15 that forms a hermetic seal that protects internal components of ICD 14. The housing 15 of ICD 14 may be formed of a conductive material, such as titanium or titanium alloy. The housing 15 may function as an electrode (sometimes referred to as a "can" electrode). Housing 15 may be used as an active can electrode for use in delivering CV/DF shocks or other high voltage pulses delivered using a high voltage therapy circuit. In other examples, housing 15 may be available for use in delivering unipolar, low voltage cardiac pacing pulses and/or for sensing cardiac electrical signals in combination with electrodes carried by lead 16. In other instances, the housing 15 of ICD 14 may include a plurality of electrodes on an outer portion of the housing. The outer portion(s) of the housing 15 functioning as an electrode(s) may be coated with a material, such as titanium nitride, e.g., for reducing post-stimulation polarization artifact.

ICD 14 includes a connector assembly 17 (also referred to as a connector block or header) that includes electrical feedthroughs crossing housing 15 to provide electrical connections between conductors extending within the lead body 18 of lead 16 and electronic components included within the housing 15 of ICD 14. As will be described in further detail herein, housing 15 may house one or more processors, memories, transceivers, cardiac electrical signal sensing circuitry, therapy delivery circuitry, power sources and other components for sensing cardiac electrical signals, detecting a heart rhythm, and controlling and delivering electrical stimulation pulses to treat an abnormal heart rhythm.

Elongated lead body 18 has a proximal end 27 that includes a lead connector (not shown) configured to be connected to ICD connector assembly 17 and a distal portion 25 that includes one or more electrodes. In the example illustrated in FIGS. 1A and 1B, the distal portion 25 of lead body 18 includes defibrillation electrodes 24 and 26 and pace/sense electrodes 28 and 30. In some cases, defibrillation electrodes 24 and 26 may together form a defibrillation electrode in that they may be configured to be activated concurrently. Alternatively, defibrillation electrodes 24 and 26 may form separate defibrillation electrodes in which case each of the electrodes 24 and 26 may be activated independently.

Electrodes 24 and 26 (and in some examples housing 15) are referred to herein as defibrillation electrodes because they are utilized, individually or collectively, for delivering high voltage stimulation therapy (e.g., cardioversion or defibrillation shocks). Electrodes 24 and 26 may be elongated coil electrodes and generally have a relatively high surface area for delivering high voltage electrical stimulation pulses compared to pacing and sensing electrodes 28 and 30. However, electrodes 24 and 26 and housing 15 may also be utilized to provide pacing functionality, sensing functionality or both pacing and sensing functionality in addition to or instead of high voltage stimulation therapy. In this sense, the use of the term "defibrillation electrode" herein should not be considered as limiting the electrodes 24 and 26 for use in only high voltage cardioversion/defibrillation shock therapy applications. For example, either of electrodes 24 and 26 may be used as a sensing electrode in a sensing vector for sensing cardiac electrical signals and determining a need for an electrical stimulation therapy.

Electrodes 28 and 30 are relatively smaller surface area electrodes which are available for use in sensing electrode vectors for sensing cardiac electrical signals and may be used for delivering relatively low voltage pacing pulses in some configurations. Electrodes 28 and 30 are referred to as pace/sense electrodes because they are generally configured for use in low voltage applications, e.g., used as either a cathode or anode for delivery of pacing pulses and/or sensing of cardiac electrical signals, as opposed to delivering high voltage CV/DF shocks. In some instances, electrodes 28 and 30 may provide only pacing functionality, only sensing functionality or both.

ICD 14 may obtain cardiac electrical signals corresponding to electrical activity of heart 8 via a combination of sensing electrode vectors that include combinations of electrodes 24, 26, 28 and/or 30. In some examples, housing 15 of ICD 14 is used in combination with one or more of electrodes 24, 26, 28 and/or 30 in a sensing electrode vector. Various sensing electrode vectors utilizing combinations of electrodes 24, 26, 28, and 30 and housing 15 are described below for acquiring first and second cardiac electrical signals using respective first and second sensing electrode vectors that may be selected by sensing circuitry included in ICD 14.

In the example illustrated in FIGS. 1A and 1B, electrode 28 is located proximal to defibrillation electrode 24, and electrode 30 is located between defibrillation electrodes 24 and 26. One, two or more pace/sense electrodes may be carried by lead body 18. For instance, a third pace/sense electrode may be located distal to defibrillation electrode 26 in some examples. Electrodes 28 and 30 are illustrated as ring electrodes; however, electrodes 28 and 30 may comprise any of a number of different types of electrodes, including ring electrodes, short coil electrodes, hemispherical electrodes, directional electrodes, segmented electrodes, or the like. Electrodes 28 and 30 may be positioned at other locations along lead body 18 and are not limited to the positions shown. In other examples, lead 16 may include fewer or more pace/sense electrodes and/or defibrillation electrodes than the example shown here.

In the example shown, lead 16 extends subcutaneously or submuscularly over the ribcage 32 medially from the connector assembly 27 of ICD 14 toward a center of the torso of patient 12, e.g., toward xiphoid process 20 of patient 12. At a location near xiphoid process 20, lead 16 bends or turns and extends superiorly, subcutaneously or submuscularly, over the ribcage and/or sternum, substantially parallel to sternum 22. Although illustrated in FIG. 1A as being offset laterally from and extending substantially parallel to sternum 22, the distal portion 25 of lead 16 may be implanted at other locations, such as over sternum 22, offset to the right or left of sternum 22, angled laterally from sternum 22 toward the left or the right, or the like. Alternatively, lead 16 may be placed along other subcutaneous or submuscular paths. The path of extra-cardiovascular lead 16 may depend on the location of ICD 14, the arrangement and position of electrodes carried by the lead body 18, and/or other factors.

Electrical conductors (not illustrated) extend through one or more lumens of the elongated lead body 18 of lead 16 from the lead connector at the proximal lead end 27 to electrodes 24, 26, 28, and 30 located along the distal portion 25 of the lead body 18. The elongated electrical conductors contained within the lead body 18, which may be separate respective insulated conductors within the lead body 18, are each electrically coupled with respective defibrillation electrodes 24 and 26 and pace/sense electrodes 28 and 30. The respective conductors electrically couple the electrodes 24, 26, 28, and 30 to circuitry, such as a therapy delivery circuit and/or a sensing circuit, of ICD 14 via connections in the connector assembly 17, including associated electrical feedthroughs crossing housing 15. The electrical conductors transmit therapy from a therapy delivery circuit within ICD 14 to one or more of defibrillation electrodes 24 and 26 and/or pace/sense electrodes 28 and 30 and transmit sensed electrical signals produced by the patient's heart 8 from one or more of defibrillation electrodes 24 and 26 and/or pace/sense electrodes 28 and 30 to the sensing circuit within ICD 14.

The lead body 18 of lead 16 may be formed from a non-conductive material, including silicone, polyurethane, fluoropolymers, mixtures thereof, and/or other appropriate materials, and shaped to form one or more lumens within which the one or more conductors extend. Lead body 18 may be tubular or cylindrical in shape. In other examples, the distal portion 25 (or all of) the elongated lead body 18 may have a flat, ribbon or paddle shape. Lead body 18 may be formed having a preformed distal portion 25 that is generally straight, curving, bending, serpentine, undulating or zig-zagging.

In the example shown, lead body 18 includes a curving distal portion 25 having two "C" shaped curves, which together may resemble the Greek letter epsilon, "ε." Defibrillation electrodes 24 and 26 are each carried by one of the two respective C-shaped portions of the lead body distal portion 25. The two C-shaped curves are seen to extend or curve in the same direction away from a central axis of lead body 18, along which pace/sense electrodes 28 and 30 are positioned. Pace/sense electrodes 28 and 30 may, in some instances, be approximately aligned with the central axis of the straight, proximal portion of lead body 18 such that mid-points of defibrillation electrodes 24 and 26 are laterally offset from pace/sense electrodes 28 and 30.

Other examples of extra-cardiovascular leads including one or more defibrillation electrodes and one or more pacing and sensing electrodes carried by curving, serpentine, undulating or zig-zagging distal portion of the lead body 18 that may be implemented with the techniques described herein are generally disclosed in pending U.S. Pat. Publication No. 2016/0158567 (Marshall, et al.), incorporated herein by reference in its entirety. The techniques disclosed herein are not limited to any particular lead body design, however. In other examples, lead body 18 is a flexible elongated lead body without any pre-formed shape, bends or curves.

ICD 14 analyzes the cardiac electrical signals received from one or more sensing electrode vectors to monitor for abnormal rhythms, such as bradycardia, ventricular tachycardia (VT) or ventricular fibrillation (VF). ICD 14 may analyze the heart rate and morphology of the cardiac electrical signals to monitor for tachyarrhythmia in accordance with any of a number of tachyarrhythmia detection techniques.

ICD 14 generates and delivers electrical stimulation therapy in response to detecting a tachyarrhythmia (e.g., VT or VF) using a therapy delivery electrode vector which may be selected from any of the available electrodes 24, 26, 28 30 and/or housing 15. ICD 14 may deliver anti-tachycardia pacing (ATP) in response to VT detection and in some cases may deliver ATP prior to a CV/DF shock or during high voltage capacitor charging in an attempt to avert the need for delivering a CV/DF shock. If ATP does not successfully terminate VT or when VF is detected, ICD 14 may deliver one or more CV/DF shocks via one or both of defibrillation electrodes 24 and 26 and/or housing 15. ICD 14 may deliver the CV/DF shocks using electrodes 24 and 26 individually or together as a cathode (or anode) and with the housing 15 as an anode (or cathode). ICD 14 may generate and deliver other types of electrical stimulation pulses such as post-shock pacing pulses or bradycardia pacing pulses using a pacing electrode vector that includes one or more of the electrodes 24, 26, 28, and 30 and the housing 15 of ICD 14.

ICD 14 is shown implanted subcutaneously on the left side of patient 12 along the ribcage 32. ICD 14 may, in some instances, be implanted between the left posterior axillary line and the left anterior axillary line of patient 12. ICD 14 may, however, be implanted at other subcutaneous or submuscular locations in patient 12. For example, ICD 14 may be implanted in a subcutaneous pocket in the pectoral region. In this case, lead 16 may extend subcutaneously or submuscularly from ICD 14 toward the manubrium of sternum 22 and bend or turn and extend inferiorly from the manubrium to the desired location subcutaneously or submuscularly. In yet another example, ICD 14 may be placed abdominally. Lead 16 may be implanted in other extracardiovascular locations as well. For instance, as described with respect to FIGS. 2A-2C, the distal portion 25 of lead 16 may be implanted underneath the sternum/ribcage in the substernal space. FIGS. 1A and 1B are illustrative in nature and should not be considered limiting of the practice of the techniques disclosed herein.

An external device 40 is shown in telemetric communication with ICD 14 by a communication link 42. External device 40 may include a processor 52, memory 53, display 54, user interface 56 and telemetry unit 58. Processor 52 controls external device operations and processes data and signals received from ICD 14. Display 54, which may include a graphical user interface, displays data and other information to a user for reviewing ICD operation and programmed parameters as well as cardiac electrical signals retrieved from ICD 14.

User interface 56 may include a mouse, touch screen, key pad or the like to enable a user to interact with external device 40 to initiate a telemetry session with ICD 14 for retrieving data from and/or transmitting data to ICD 14, including programmable parameters for controlling cardiac event sensing and therapy delivery. Telemetry unit 58 includes a transceiver and antenna configured for bidirectional communication with a telemetry circuit included in ICD 14 and is configured to operate in conjunction with processor 52 for sending and receiving data relating to ICD functions via communication link 42.

Communication link 42 may be established between ICD 14 and external device 40 using a radio frequency (RF) link such as BLUETOOTH®, Wi-Fi, or Medical Implant Communication Service (MICS) or other RF or communication frequency bandwidth or communication protocols. Data stored or acquired by ICD 14, including physiological signals or associated data derived therefrom, results of device diagnostics, and histories of detected rhythm episodes and delivered therapies, may be retrieved from ICD 14 by external device 40 following an interrogation command.

External device 40 may be embodied as a programmer used in a hospital, clinic or physician's office to retrieve data from ICD 14 and to program operating parameters and algorithms in ICD 14 for controlling ICD functions. External device 40 may alternatively be embodied as a home monitor or hand held device. External device 40 may be used to program cardiac signal sensing parameters, cardiac rhythm detection parameters and therapy control parameters used by ICD 14. At least some control parameters used in detecting cardiac event oversensing according to techniques disclosed herein may be programmed into ICD 14 using external device 40 in some examples.

Figure 2A:
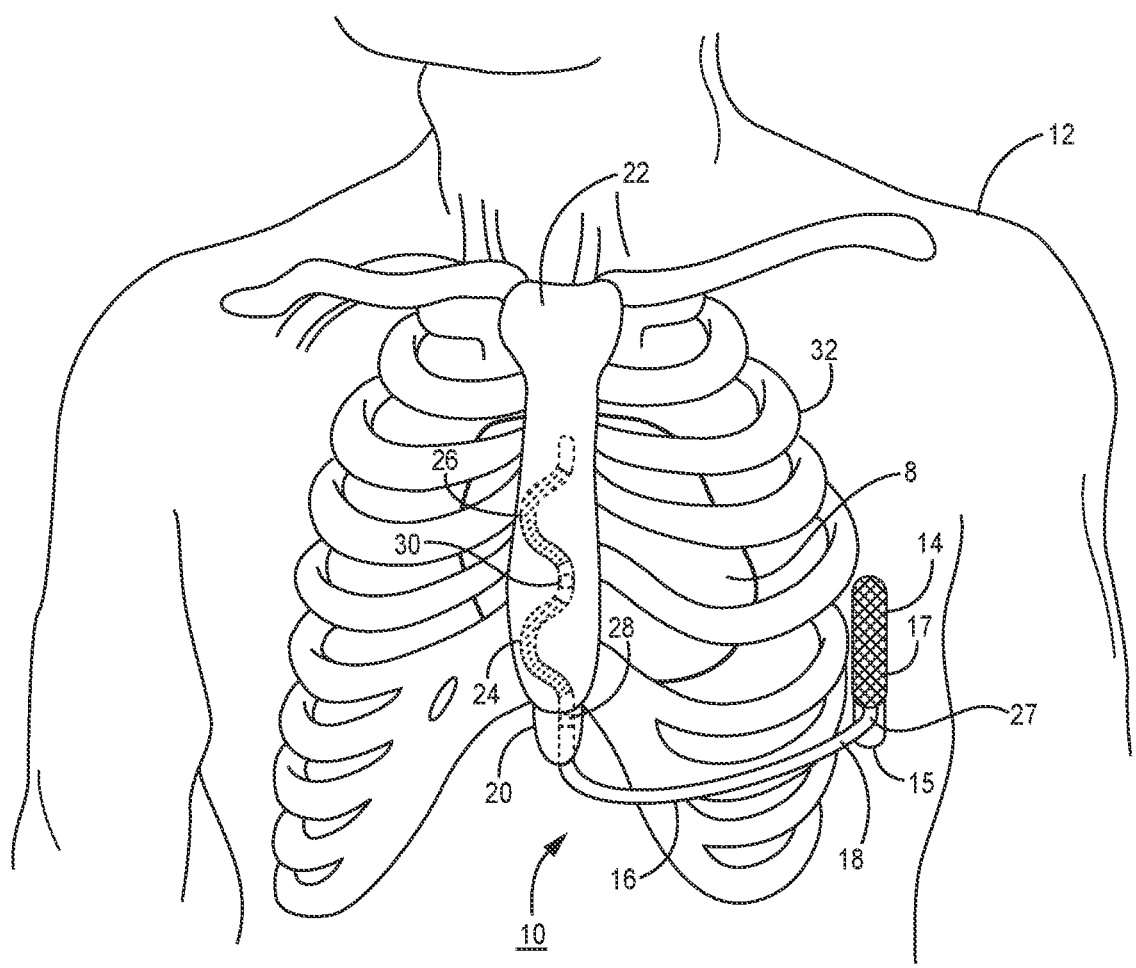
FIGS. 2A-2C are conceptual diagrams of a patient implanted with an extra-cardiovascular ICD system in a different implant configuration than the arrangement shown in FIGS. 1A-1B.
Figure 2B:
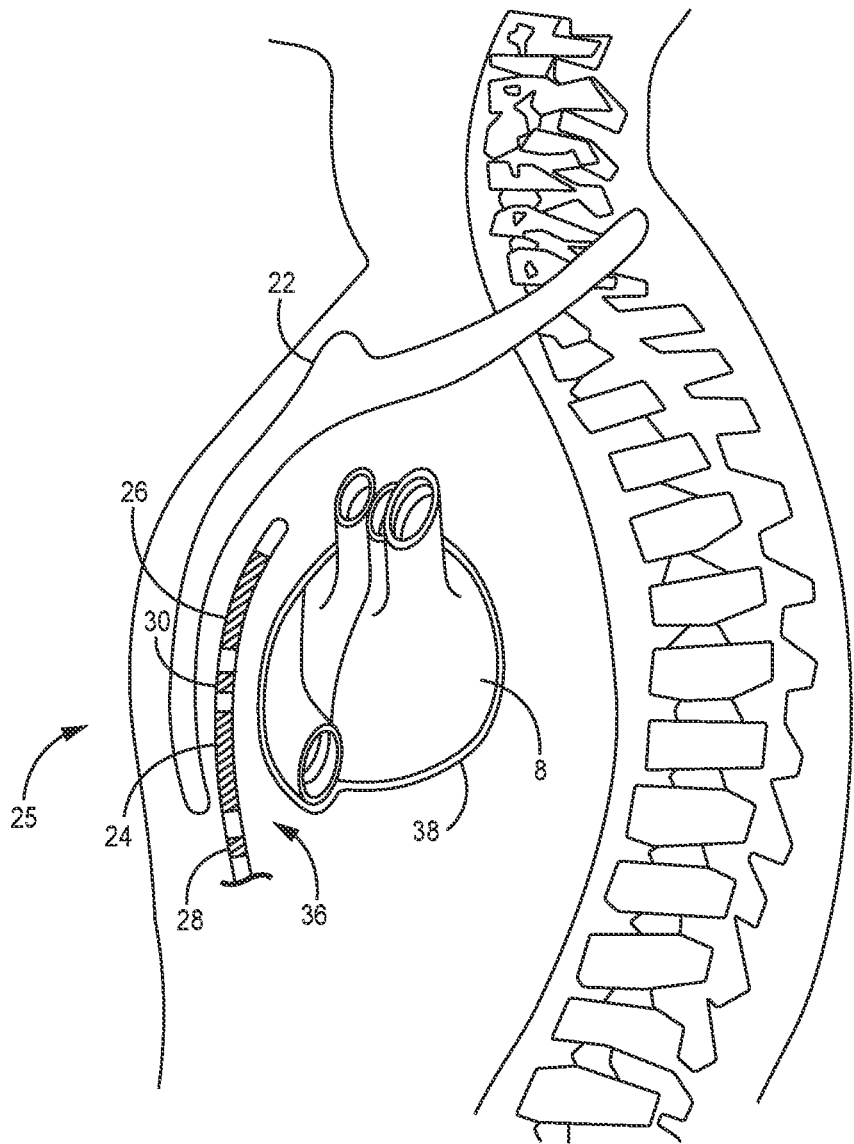
Figure 2C:
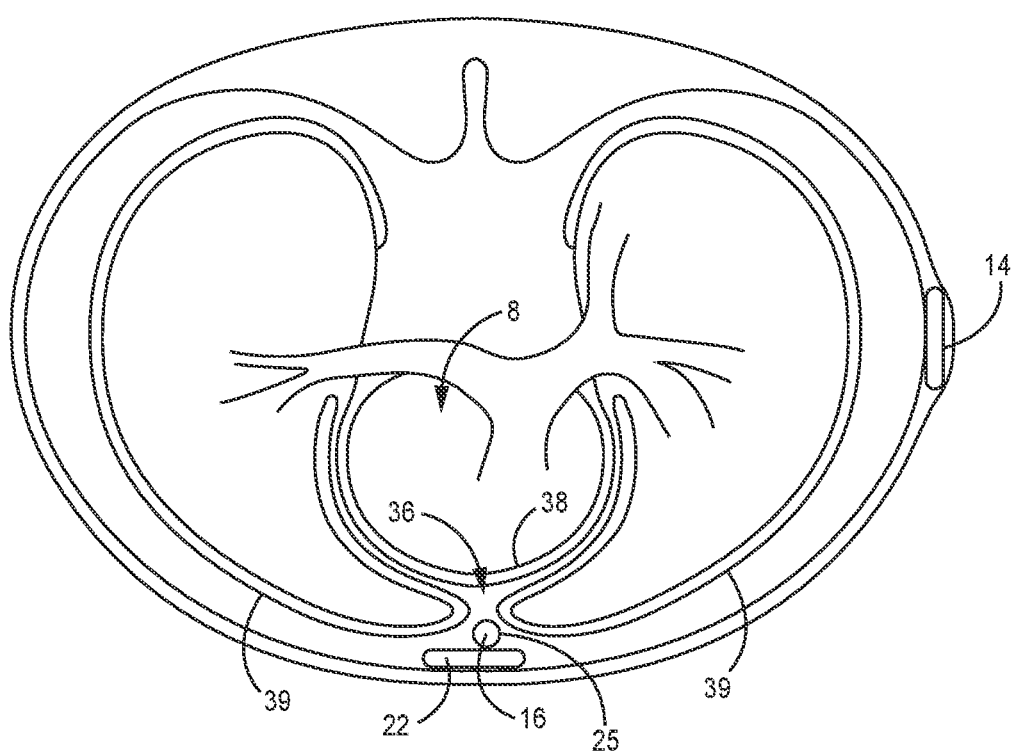

FIGS. 2A-2C are conceptual diagrams of patient 12 implanted with extra-cardiovascular ICD system 10 in a different implant configuration than the arrangement shown in FIGS. 1A-1B. FIG. 2A is a front view of patient 12 implanted with ICD system 10. FIG. 2B is a side view of patient 12 implanted with ICD system 10. FIG. 2C is a transverse view of patient 12 implanted with ICD system 10. In this arrangement, extra-cardiovascular lead 16 of system 10 is implanted at least partially underneath sternum 22 of patient 12. Lead 16 extends subcutaneously or submuscularly from ICD 14 toward xiphoid process 20 and at a location near xiphoid process 20 bends or turns and extends superiorly within anterior mediastinum 36 in a substernal position.

Anterior mediastinum 36 may be viewed as being bounded laterally by pleurae 39, posteriorly by pericardium 38, and anteriorly by sternum 22 (see FIG. 2C). The distal portion 25 of lead 16 may extend along the posterior side of sternum 22 substantially within the loose connective tissue and/or substernal musculature of anterior mediastinum 36. A lead implanted such that the distal portion 25 is substantially within anterior mediastinum 36, may be referred to as a "substernal lead."

In the example illustrated in FIGS. 2A-2C, lead 16 is located substantially centered under sternum 22. In other instances, however, lead 16 may be implanted such that it is offset laterally from the center of sternum 22. In some instances, lead 16 may extend laterally such that distal portion 25 of lead 16 is underneath/below the ribcage 32 in addition to or instead of sternum 22. In other examples, the distal portion 25 of lead 16 may be implanted in other extra-cardiovascular, intra-thoracic locations, including the pleural cavity or around the perimeter of and adjacent to the pericardium 38 of heart 8.

Figure 3:
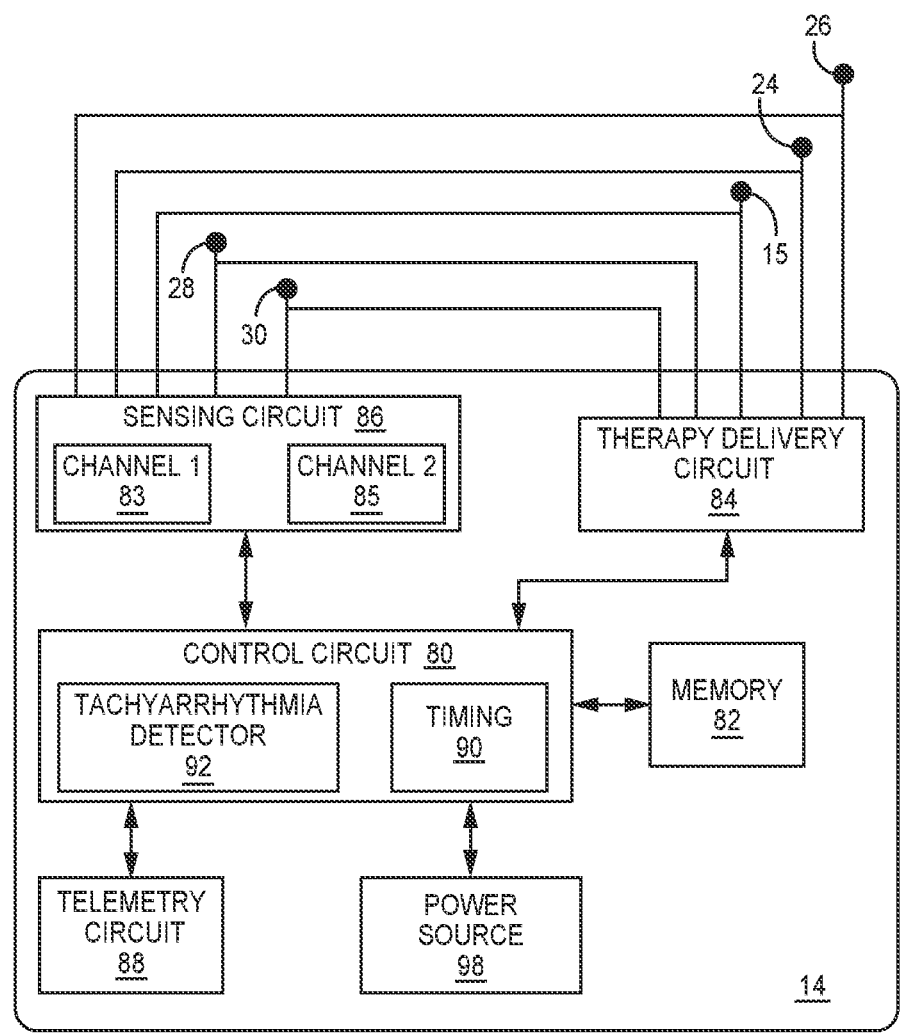
FIG. 3 is a schematic diagram of an ICD according to one example.

FIG. 3 is a schematic diagram of ICD 14 according to one example. The electronic circuitry enclosed within housing 15 (shown schematically as an electrode in FIG. 3) includes software, firmware and hardware that cooperatively monitor cardiac electrical signals, determine when an electrical stimulation therapy is necessary, and deliver therapy as needed according to programmed therapy delivery algorithms and control parameters. ICD 14 may be coupled to an extra-cardiovascular lead, such as lead 16 carrying extra-cardiovascular electrodes 24, 26, 28, and 30, for delivering electrical stimulation pulses to the patient's heart and for sensing cardiac electrical signals.

ICD 14 includes a control circuit 80, memory 82, therapy delivery circuit 84, cardiac electrical signal sensing circuit 86, and telemetry circuit 88. A power source 98 provides power to the circuitry of ICD 14, including each of the components 80, 82, 84, 86, and 88 as needed. Power source 98 may include one or more energy storage devices, such as one or more rechargeable or non-rechargeable batteries. The connections between power source 98 and each of the other components 80, 82, 84, 86 and 88 are to be understood from the general block diagram of FIG. 3, but are not shown for the sake of clarity. For example, power source 98 may be coupled to one or more charging circuits included in therapy delivery circuit 84 for charging holding capacitors included in therapy delivery circuit 84 that are discharged at appropriate times under the control of control circuit 80 for producing electrical pulses according to a therapy protocol. Power source 98 is also coupled to components of cardiac electrical signal sensing circuit 86, such as sense amplifiers, analog-to-digital converters, switching circuitry, etc. as needed.

The circuits shown in FIG. 3 represent functionality included in ICD 14 and may include any discrete and/or integrated electronic circuit components that implement analog and/or digital circuits capable of producing the functions attributed to ICD 14 herein. Functionality associated with one or more circuits may be performed by separate hardware, firmware or software components, or integrated within common hardware, firmware or software components. For example, cardiac event sensing and detection of oversensing cardiac events may be performed cooperatively by sensing circuit 86 and control circuit 80 and may include operations implemented in a processor or other signal processing circuitry included in control circuit 80 executing instructions stored in memory 82 and control signals such as blanking and timing intervals and sensing threshold amplitude signals sent from control circuit 80 to sensing circuit 86.

The various circuits of ICD 14 may include an application specific integrated circuit (ASIC), an electronic circuit, a processor (shared, dedicated, or group) and memory that execute one or more software or firmware programs, a combinational logic circuit, state machine, or other suitable components or combinations of components that provide the described functionality. The particular form of software, hardware and/or firmware employed to implement the functionality disclosed herein will be determined primarily by the particular system architecture employed in the ICD and by the particular detection and therapy delivery methodologies employed by the ICD. Providing software, hardware, and/or firmware to accomplish the described functionality in the context of any modern implantable cardiac device system, given the disclosure herein, is within the abilities of one of skill in the art.

Memory 82 may include any volatile, non-volatile, magnetic, or electrical non-transitory computer readable storage media, such as random access memory (RAM), read-only memory (ROM), non-volatile RAM (NVRAM), electrically-erasable programmable ROM (EEPROM), flash memory, or any other memory device. Furthermore, memory 82 may include non-transitory computer readable media storing instructions that, when executed by one or more processing circuits, cause control circuit 80 and/or other ICD components to perform various functions attributed to ICD 14 or those ICD components. The non-transitory computer-readable media storing the instructions may include any of the media listed above.

Control circuit 80 communicates, e.g., via a data bus, with therapy delivery circuit 84 and sensing circuit 86 for sensing cardiac electrical activity, detecting cardiac rhythms, and controlling delivery of cardiac electrical stimulation therapies in response to sensed cardiac signals. Therapy delivery circuit 84 and sensing circuit 86 are electrically coupled to electrodes 24, 26, 28, 30 carried by lead 16 and the housing 15, which may function as a common or ground electrode or as an active can electrode for delivering CV/DF shock pulses or cardiac pacing pulses.

Sensing circuit 86 may be selectively coupled to electrodes 28, 30 and/or housing 15 in order to monitor electrical activity of the patient's heart. Sensing circuit 86 may additionally be selectively coupled to defibrillation electrodes 24 and/or 26 for use in a sensing electrode vector together or in combination with one or more of electrodes 28, 30 and/or housing 15. Sensing circuit 86 may be enabled to selectively receive cardiac electrical signals from at least two sensing electrode vectors from the available electrodes 24, 26, 28, 30, and housing 15. At least two cardiac electrical signals from two different sensing electrode vectors may be received simultaneously by sensing circuit 86 in some examples. Sensing circuit 86 may monitor one or both of the cardiac electrical signals simultaneously for sensing cardiac electrical events and/or producing digitized cardiac signal waveforms for analysis by control circuit 80. For example, sensing circuit 86 may include switching circuitry for selecting which of electrodes 24, 26, 28, 30, and housing 15 are coupled to a first sensing channel 83 and which electrodes are coupled to a second sensing channel 85 of sensing circuit 86.

Each sensing channel 83 and 85 may be configured to amplify, filter and digitize the cardiac electrical signal received from selected electrodes coupled to the respective sensing channel to improve the signal quality for detecting cardiac electrical events, such as R-waves or performing other signal analysis. The cardiac event detection circuitry within sensing circuit 86 may include one or more sense amplifiers, filters, rectifiers, threshold detectors, comparators, analog-to-digital converters (ADCs), timers or other analog or digital components as described further in conjunction with FIG. 4. A cardiac event sensing threshold may be automatically adjusted by sensing circuit 86 under the control of control circuit 80, based on timing intervals and sensing threshold values determined by control circuit 80, stored in memory 82, and/or controlled by hardware, firmware and/or software of control circuit 80 and/or sensing circuit 86.

Upon detecting a cardiac event based on a sensing threshold crossing, first sensing channel 83 may produce a sensed event signal, such as an R-wave sensed event signal, that is passed to control circuit 80. The sensed event signal is used by control circuit 80 to trigger storage of a time segment of a cardiac electrical signal for post-processing and analysis for detecting cardiac event oversensing as described below, e.g., in conjunction with FIGS. 5 through 9. In some examples, sensing circuit 86 senses at least one cardiac electrical signal received by a sensing electrode vector selected from the available electrodes, e.g., electrodes 24, 26, 28, 30 and housing 15, for detecting R-waves and buffering multiple cardiac electrical signal segments, where each cardiac electrical signal segment corresponds to a detected R-wave, for processing and analysis for detecting P-wave oversensing. A single cardiac electrical signal sensed by first sensing channel 83 may be used for both R-wave detection and analysis of cardiac electrical signal segments for PWOS detection. In other examples, R-waves are detected from the first cardiac electrical signal sensed by the first sensing channel 83 and segments of a second cardiac electrical signal sensed by the second sensing channel 85 may be buffered, with each segment corresponding to an R-wave sensed from the first cardiac electrical signal. PWOS detection may be based on the analysis of the second cardiac electrical signal segments. The second cardiac electrical signal may be received via a different sensing electrode pair coupled to the second sensing channel 85 than the sensing electrode pair coupled to the first sensing channel 83 for sensing the first cardiac electrical signal, and/or the second cardiac electrical signal may be received by the same sensing electrode pair but processed differently, e.g., filtered differently, by the second sensing channel 85 to produce a second cardiac electrical signal sensed by sensing circuit 86 different than the first cardiac electrical signal.

Memory 82 may be configured to store a predetermined number of cardiac electrical signal segments in a circulating buffer under the control of control circuit 80, e. g., at least one, two, three or other number of cardiac electrical signal segments. Each segment may be written to memory 82 over a time interval extending before and after an R-wave sensed event signal produced by the first sensing channel 83. Control circuit 80 may access stored cardiac electrical signal segments when confirmation of R-waves sensed by the first sensing channel 83 is required based on the detection of a predetermined number of tachyarrhythmia intervals, which may precede tachyarrhythmia detection.

The R-wave sensed event signals are also used by control circuit 80 for determining RR intervals (RRIs) for detecting tachyarrhythmia and determining a need for therapy. An RRI is the time interval between consecutively sensed R-waves and may be determined between consecutive R-wave sensed event signals received from sensing circuit 86. For example, control circuit 80 may include a timing circuit 90 for determining RRIs between consecutive R-wave sensed event signals received from sensing circuit 86 and for controlling various timers and/or counters used to control the timing of therapy delivery by therapy delivery circuit 84. Timing circuit 90 may additionally set time windows such as morphology template windows, morphology analysis windows or perform other timing related functions of ICD 14 including synchronizing cardioversion shocks or other therapies delivered by therapy delivery circuit 84 with sensed cardiac events.

Control circuit 80 is also shown to include a tachyarrhythmia detector 92 configured to analyze signals received from sensing circuit 86 for detecting tachyarrhythmia. Tachyarrhythmia detector 92 may detect tachyarrhythmia based on cardiac events detected from a sensed cardiac electrical signal meeting tachyarrhythmia criteria, such as a threshold number of detected cardiac events occurring at a tachyarrhythmia interval. Tachyarrhythmia detector 92 may be implemented in control circuit 80 as hardware, software and/or firmware that processes and analyzes signals received from sensing circuit 86 for detecting VT and/or VF. In some examples, the timing of R-wave sense event signals received from sensing circuit 86 is used by timing circuit 90 to determine RRIs between sensed event signals. Tachyarrhythmia detector 92 may include comparators and counters for counting RRIs determined by timing circuit 90 that fall into various rate detection zones for determining a ventricular rate or performing other rate- or interval-based assessment of R-wave sensed event signals for detecting and discriminating VT and VF.

For example, tachyarrhythmia detector 92 may compare the RRIs determined by timing circuit 90 to one or more tachyarrhythmia detection interval zones, such as a tachycardia detection interval zone and a fibrillation detection interval zone. RRIs falling into a detection interval zone are counted by a respective VT interval counter or VF interval counter and in some cases in a combined VT/VF interval counter included in tachyarrhythmia detector 92. The VF detection interval threshold may be set to 300 to 350 milliseconds (ms), as examples. For instance, if the VF detection interval is set to 320 ms, RRIs that are less than 320 ms are counted by the VF interval counter. When VT detection is enabled, the VT detection interval may be programmed to be in the range of 350 to 420 ms, or 400 ms as an example. In order to detect VT or VF, the respective VT or VF interval counter is required to reach a threshold number of intervals to detect (NID) the tachyarrhythmia.

As an example, the NID to detect VT may require that the VT interval counter reaches 32 VT intervals counted out of the most recent 32 consecutive RRIs. The NID to detect VF may be programmed to 18 VF intervals out of the most recent 24 consecutive RRIs or 30 VF intervals out 40 consecutive RRIs, as examples. When a VT or VF interval counter reaches a detection threshold, a ventricular tachyarrhythmia may be detected by tachyarrhythmia detector 92. The NID may be programmable and range from as low as 12 to as high as 40, with no limitation intended. VT or VF intervals may be detected consecutively or non-consecutively out of the specified number of most recent RRIs. In some cases, a combined VT/VF interval counter may count both VT and VF intervals and detect a tachyarrhythmia episode based on the fastest intervals detected when a specified NID is reached.

Tachyarrhythmia detector 92 may be configured to perform other signal analysis for determining if other detection criteria are satisfied before detecting VT or VF, such as R-wave morphology criteria, onset criteria, and noise and oversensing rejection criteria. Examples of parameters that may be determined from cardiac electrical signals received from sensing circuit 86 for detecting cardiac event oversensing that may cause withholding of a VT or VF detection are described in conjunction with FIGS. 5-9.

To support these additional analyses, sensing circuit 86 may pass a digitized electrocardiogram (ECG) signal to control circuit 80 for morphology analysis performed by tachyarrhythmia detector 92 for detecting and discriminating heart rhythms. A cardiac electrical signal from the selected sensing vector, e.g., from first sensing channel 83 and/or the second sensing channel 85, may be passed through a filter and amplifier, provided to a multiplexer and thereafter converted to a multi-bit digital signal by an analog-to-digital converter, all included in sensing circuit 86, for storage in memory 82. Memory 82 may include one or more circulating buffers to temporarily store digital cardiac electrical signal segments for analysis performed by control circuit 80. Control circuit 80 may be a microprocessor-based controller that employs digital signal analysis techniques to characterize the digitized signals stored in memory 82 to recognize and classify the patient's heart rhythm employing any of numerous signal processing methodologies for analyzing cardiac signals and cardiac event waveforms, e.g., R-waves. As described below, processing and analysis of digitized signals may include determining signal features for detecting patterns of oversensing and verifying that a tachyarrhythmia morphology is not present in cardiac electrical signal segments presenting a detected pattern of oversensing. When a tachyarrhythmia morphology is not present, and an alternating pattern of signal features is detected, a tachyarrhythmia detection based on RRIs may be withheld to inhibit a tachyarrhythmia therapy.

Therapy delivery circuit 84 includes charging circuitry, one or more charge storage devices such as one or more high voltage capacitors and/or low voltage capacitors, and switching circuitry that controls when the capacitor(s) are discharged across a selected pacing electrode vector or CV/DF shock vector. Charging of capacitors to a programmed pulse amplitude and discharging of the capacitors for a programmed pulse width may be performed by therapy delivery circuit 84 according to control signals received from control circuit 80. Control circuit 80 may include various timers or counters that control when cardiac pacing pulses are delivered. For example, timing circuit 90 may include programmable digital counters set by a microprocessor of the control circuit 80 for controlling the basic pacing time intervals associated with various pacing modes or ATP sequences delivered by ICD 14. The microprocessor of control circuit 80 may also set the amplitude, pulse width, polarity or other characteristics of the cardiac pacing pulses, which may be based on programmed values stored in memory 82.

In response to detecting VT or VF, control circuit 80 may schedule a therapy and control therapy delivery circuit 84 to generate and deliver the therapy, such as ATP and/or CV/DF therapy. Therapy can be generated by initiating charging of high voltage capacitors via a charging circuit, both included in therapy delivery circuit 84. Charging is controlled by control circuit 80 which monitors the voltage on the high voltage capacitors, which is passed to control circuit 80 via a charging control line. When the voltage reaches a predetermined value set by control circuit 80, a logic signal is generated on a capacitor full line and passed to therapy delivery circuit 84, terminating charging. A CV/DF pulse is delivered to the heart under the control of the timing circuit 90 by an output circuit of therapy delivery circuit 84 via a control bus. The output circuit may include an output capacitor through which the charged high voltage capacitor is discharged via switching circuitry, e. g., an H-bridge, which determines the electrodes used for delivering the cardioversion or defibrillation pulse and the pulse wave shape.

In some examples, the high voltage therapy circuit configured to deliver CV/DF shock pulses can be controlled by control circuit 80 to deliver pacing pulses, e.g., for delivering ATP, post shock pacing pulses or ventricular pacing pulses during atrioventricular conduction block or bradycardia. In other examples, therapy delivery circuit 84 may include a low voltage therapy circuit for generating and delivering pacing pulses for a variety of pacing needs.

It is recognized that the methods disclosed herein for detecting cardiac event oversensing may be implemented in a medical device that is used for monitoring cardiac electrical signals by sensing circuit 86 and control circuit 80 without having therapy delivery capabilities or in a pacemaker that monitors cardiac electrical signals and delivers cardiac pacing therapies by therapy delivery circuit 84, without high voltage therapy capabilities, such as cardioversion/defibrillation shock capabilities.

Control parameters utilized by control circuit 80 for sensing cardiac events and controlling therapy delivery may be programmed into memory 82 via telemetry circuit 88. Telemetry circuit 88 includes a transceiver and antenna for communicating with external device 40 (shown in FIG. 1A) using RF communication or other communication protocols as described above. Under the control of control circuit 80, telemetry circuit 88 may receive downlink telemetry from and send uplink telemetry to external device 40.

Figure 4:
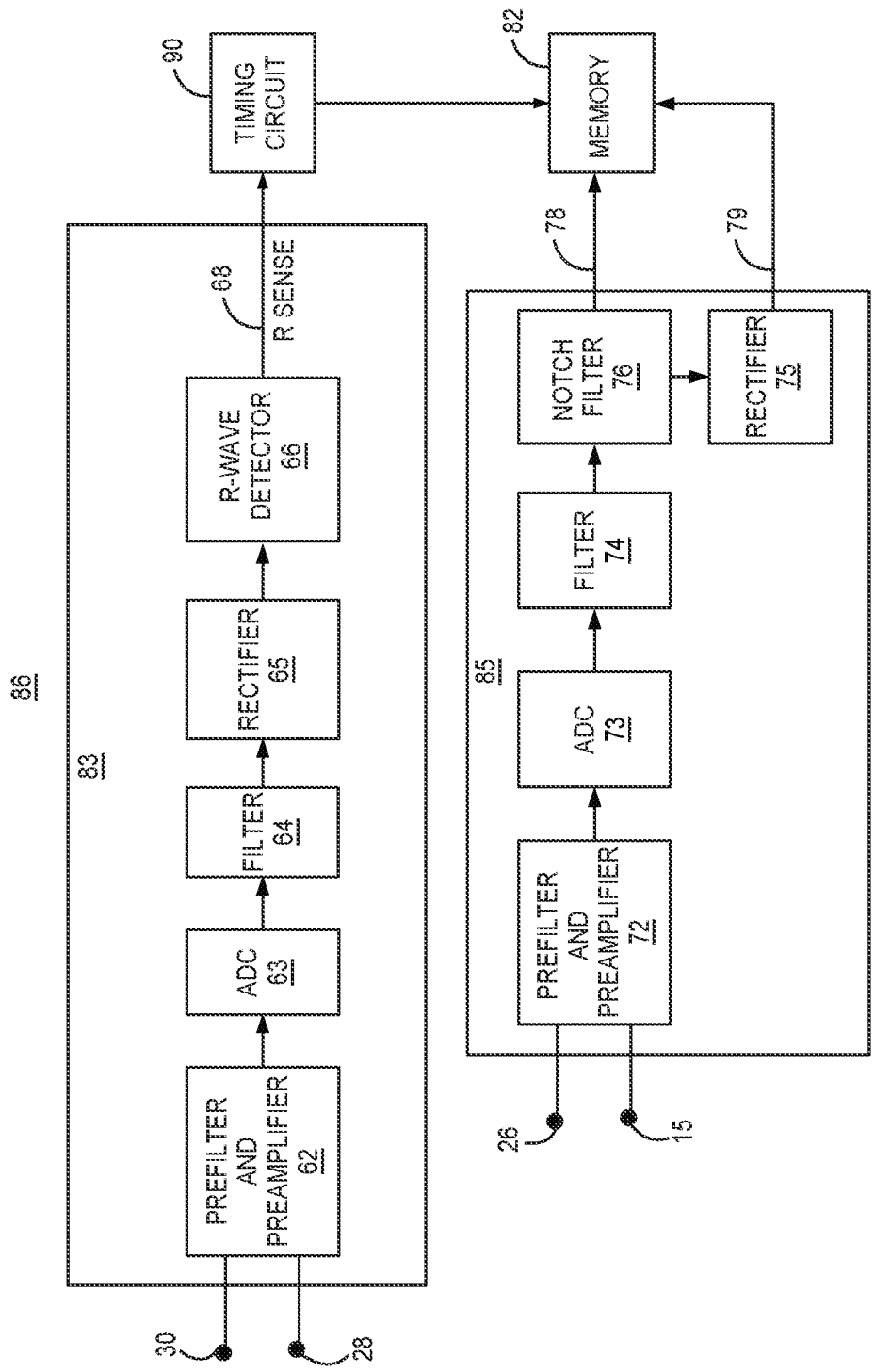
FIG. 4 is a diagram of circuitry included in a sensing circuit of the ICD of FIG. 3.

FIG. 4 is a diagram of circuitry included in sensing circuit 86 having first sensing channel 83 and second sensing channel 85 according to one example. First sensing channel 83 may be selectively coupled via switching circuitry included in sensing circuit 86 to a first sensing electrode vector including at least one electrode carried by extra-cardiovascular lead 16 for receiving a first cardiac electrical signal. In some examples, first sensing channel 83 may be coupled to a sensing electrode vector that is a short bipole, having a relatively shorter inter-electrode distance or spacing than the second electrode vector coupled to second sensing channel 85. First sensing channel 83 may be coupled to a sensing electrode vector that is approximately vertical (when the patient is in an upright position) or approximately aligned with the cardiac axis to increase the likelihood of a relatively high R-wave signal amplitude relative to P-wave signal amplitude. In one example, the first sensing electrode vector may include pace/sense electrodes 28 and 30. In other examples, the first sensing electrode vector coupled to sensing channel 83 may include a defibrillation electrode 24 and/or 26, e.g., a sensing electrode vector between pace/sense electrode 28 and defibrillation electrode 24 or between pace/sense electrode 30 and either of defibrillation electrodes 24 or 26. In still other examples, the first sensing electrode vector may be between defibrillation electrodes 24 and 26.

Sensing circuit 86 includes second sensing channel 85 for sensing a second cardiac electrical signal in some examples. For instance, second sensing channel 85 may receive a raw cardiac electrical signal from a second sensing electrode vector, for example from a vector that includes one electrode 24, 26, 28 or 30 carried by lead 16 paired with housing 15. Second sensing channel 85 may be selectively coupled to other sensing electrode vectors, which may form a relatively longer bipole having an inter-electrode distance or spacing that is greater than the sensing electrode vector coupled to first sensing channel 83 in some examples. The second sensing electrode vector may be, but not necessarily, approximately orthogonal to the first channel sensing electrode vector in some cases. For instance, defibrillation electrode 26 and housing 15 may be coupled to second sensing channel 85 to provide the second cardiac electrical signal. As described below, the second cardiac electrical signal received by second sensing channel 85 via a long bipole may be used by control circuit 80 for analysis and detection of P-wave oversensing (when atrial P-waves are falsely sensed as R-waves by the first sensing channel 83). The long bipole coupled to second sensing channel 85 may provide a relatively far-field or more global cardiac signal compared to the relatively shorter bipole coupled to the first sensing channel. In the relatively more global signal, the amplitude of P-waves may be relatively higher or lower (depending on the location of the electrodes relative to atrium) than in the more near-field signal received by the first sensing channel 83 and used for sensing R-waves for determining RRIs. In other examples, any vector selected from the available electrodes, e.g., electrodes 24, 26, 28, 30 and/or housing 15, may be included in a sensing electrode vector coupled to second sensing channel 85. The sensing electrode vectors coupled to first sensing channel 83 and second sensing channel 85 may be different sensing electrode vectors, which may have no common electrodes or only one common electrode but not both.

In other examples, however, the sensing electrode vectors coupled to the first sensing channel 83 and the second sensing channel 85 may be the same sensing electrode vectors. The two sensing channels 83 and 85 may include different filters or other signal processing circuitry such that two different signals are sensed by the respective sensing channels and different analyses may be performed on the two signals. For example, the first sensing channel 83 may sense a first cardiac electrical signal by filtering and processing the received cardiac electrical signal for detecting R-waves in response to an R-wave sensing threshold crossing for determining RRIs. The second sensing channel 85 may sense a second cardiac electrical signal different than the first by filtering and processing the received cardiac electrical signal for passing signal segments to control circuit 80 for determination and analysis of signal waveform morphology and specific morphological features for detecting alternating signal features and detecting segments having a tachyarrhythmia morphology. The first sensing channel 83 may apply relatively narrower band pass filtering, and the second sensing channel 85 may apply relatively wider band pass filtering and notch filtering to provide two different sensed cardiac electrical signals.

In the illustrative example shown in FIG. 4, the electrical signals developed across the first sensing electrode vector, e.g., electrodes 28 and 30, are received by first sensing channel 83 and electrical signals developed across the second sensing electrode vector, e.g., electrodes 26 and housing 15, are received by second sensing channel 85. The cardiac electrical signals are provided as differential input signals to the pre-filter and pre-amplifier 62 or 72, respectively, of first sensing channel 83 and second sensing channel 85. Non-physiological high frequency and DC signals may be filtered by a low pass or bandpass filter included in each of pre-filter and pre-amplifiers 62 and 72, and high voltage signals may be removed by protection diodes included in pre-filter and pre-amplifiers 62 and 72. Pre-filter and pre-amplifiers 62 and 72 may amplify the pre-filtered signal by a gain of between 10 and 100, and in one example a gain of 17.5, and may convert the differential signal to a single-ended output signal passed to analog-to-digital converter (ADC) 63 in first sensing channel 83 and to ADC 73 in second sensing channel 85. Pre-filters and amplifiers 62 and 72 may provide anti-alias filtering and noise reduction prior to digitization.

ADC 63 and ADC 73, respectively, convert the first cardiac electrical signal from an analog signal to a first digital bit stream and the second cardiac electrical signal to a second digital bit stream. In one example, ADC 63 and ADC 73 may be sigma-delta converters (SDC), but other types of ADCs may be used. In some examples, the outputs of ADC 63 and ADC 73 may be provided to decimators (not shown), which function as digital low-pass filters that increase the resolution and reduce the sampling rate of the respective first and second cardiac electrical signals.

The digital outputs of ADC 63 and ADC 73 are each passed to respective filters 64 and 74, which may be digital bandpass filters. The bandpass filters 64 and 74 may have the same or different bandpass frequencies. For example, filter 64 may have a bandpass of approximately 13 Hz to 39 Hz for passing cardiac electrical signals such as R-waves typically occurring in this frequency range. Filter 74 of the second sensing channel 85 may have a bandpass of approximately 2.5 to 100 Hz. In some examples, second sensing channel 85 may further include a notch filter 76 to filter 60 Hz or 50 Hz noise signals.

The bandpass filtered signal in first sensing channel 83 is passed from filter 64 to rectifier 65 to produce a filtered, rectified signal. First sensing channel 83 includes an R-wave detector 66 for sensing cardiac events in response to the first cardiac electrical signal crossing an R-wave sensing threshold. R-wave detector 66 may include an auto-adjusting sense amplifier, comparator and/or other detection circuitry that compares the filtered and rectified cardiac electrical signal to an R-wave sensing threshold in real time and produces an R-wave sensed event signal 68 when the cardiac electrical signal crosses the R-wave sensing threshold outside of a post-sense blanking interval. The R-wave sensing threshold may be a multi-level sensing threshold as disclosed in commonly assigned U.S. Pat. No. 10,252,071 (Cao, et al.), incorporated herein by reference in its entirety. Briefly, the multi-level sensing threshold may have a starting sensing threshold value held for a time interval, which may be equal to a tachycardia detection interval or expected R-wave to T-wave interval, then drops to a second sensing threshold value held until a drop time interval expires, which may be 1 to 2 seconds long. The sensing threshold drops to a minimum sensing threshold, which may correspond to a programmed sensitivity sometimes referred to as the "sensing floor," after the drop time interval. In other examples, the R-wave sensing threshold used by R-wave detector 66 may be set to a starting value based on the peak amplitude determined during the most recent post-sense blanking interval and decay linearly or exponentially over time until reaching a minimum sensing threshold. The techniques described herein are not limited to a specific behavior of the sensing threshold or specific R-wave sensing techniques. Instead, other decaying, step-wise adjusted or other automatically adjusted sensing thresholds may be utilized.

The notch-filtered, digital cardiac electrical signal 78 from second sensing channel 85 may be passed to memory 82 for buffering a segment of the second cardiac electrical signal 78 in response to an R-wave sensed event signals 68 produced by the first sensing channel 83. In some examples, the buffered segment of the second cardiac electrical signal 78 is rectified by rectifier 75 before being stored in memory 82. In some cases, both the filtered, non-rectified signal 78 and the rectified signal 79 are passed to control circuit 80 and/or memory 82 for use in determining features of multiple segments of the second cardiac electrical signal, where each segment extends over a time interval that encompasses the time point of an R-wave sensed event signal produced by the first sensing channel 83.

Control circuit 80 is configured to detect tachyarrhythmia based on cardiac events detected from at least one cardiac electrical signal sensed by sensing circuit 86. For example, control circuit 80 may be configured to detect tachyarrhythmia when a threshold number of detected cardiac events each occur at a tachyarrhythmia interval. Control circuit 80 may buffer segments of a sensed cardiac electrical signal in memory 82 and retrieve stored signal segments from memory 82 for analysis when a lower threshold number of tachyarrhythmia intervals have been detected, before the detection threshold is reached. In some examples, the RRIs for detecting tachyarrhythmia intervals are determined from the first cardiac electrical signal sensed by first sensing channel 83, and cardiac electrical signal segments are buffered from the second cardiac electrical signal received by control circuit 80 from second sensing channel 85 for P-wave oversensing analysis when the lower threshold number of tachyarrhythmia intervals is detected. Analysis of the second cardiac electrical signal segments may be performed for use in detecting P-wave oversensing as described below in conjunction with FIGS. 5-9. In other examples, a single cardiac electrical signal sensed by sensing circuit 86 is used to both determine RRIs for detecting tachyarrhythmia intervals and buffer cardiac electrical signal segments. The buffered cardiac electrical signal segments are analyzed for detecting evidence of cardiac event oversensing.

For instance, control circuit 80 may be configured to determine a signal feature from each of multiple, consecutive second cardiac electrical signal segments for detecting an alternating pattern of the signal feature as evidence of PWOS. When evidence of PWOS is detected based on the alternating pattern of the determined signal feature, additional analysis may be performed on at least one of the second cardiac electrical signal segments of the alternating pattern to detect a tachyarrhythmia morphology present in the segment. Time segments of the notch-filtered, rectified signal 79 received from second sensing channel 85 may be used to detect a tachyarrhythmia morphology. In some examples, as described below, at least one segment of the second cardiac electrical signal that corresponds to a suspected true R-wave, based on the detected alternating pattern of the signal feature, is identified. When a tachyarrhythmia morphology is not detected in second cardiac electrical signal segment(s) identified as a suspected true R-wave in an alternating pattern, evidence of PWOS is detected. A threshold number of PWOS evidence detections may cause control circuit 80 to withhold a tachyarrhythmia detection and therapy delivery circuit 84 to withhold a tachyarrhythmia therapy.

The configuration of sensing channels 83 and 85 as shown in FIG. 4 is illustrative in nature and should not be considered limiting of the techniques described herein. The sensing channels 83 and 85 of sensing circuit 86 may include more or fewer components than illustrated and described in FIG. 4 and some components may be shared between sensing channels 83 and 85. For example, one or more of pre-filter and pre-amplifiers 62/72, ADC 63/73, and/or filters 64/74 may be shared components between sensing channels 83 and 85 with a single, sensed signal output split to two sensing channels for subsequent processing and analysis. Sensing circuit 86 and control circuit 80 include circuitry configured to perform the functionality attributed to ICD 14 in detecting cardiac event oversensing and rejecting or withholding tachyarrhythmia detection as disclosed herein.

Figure 5:
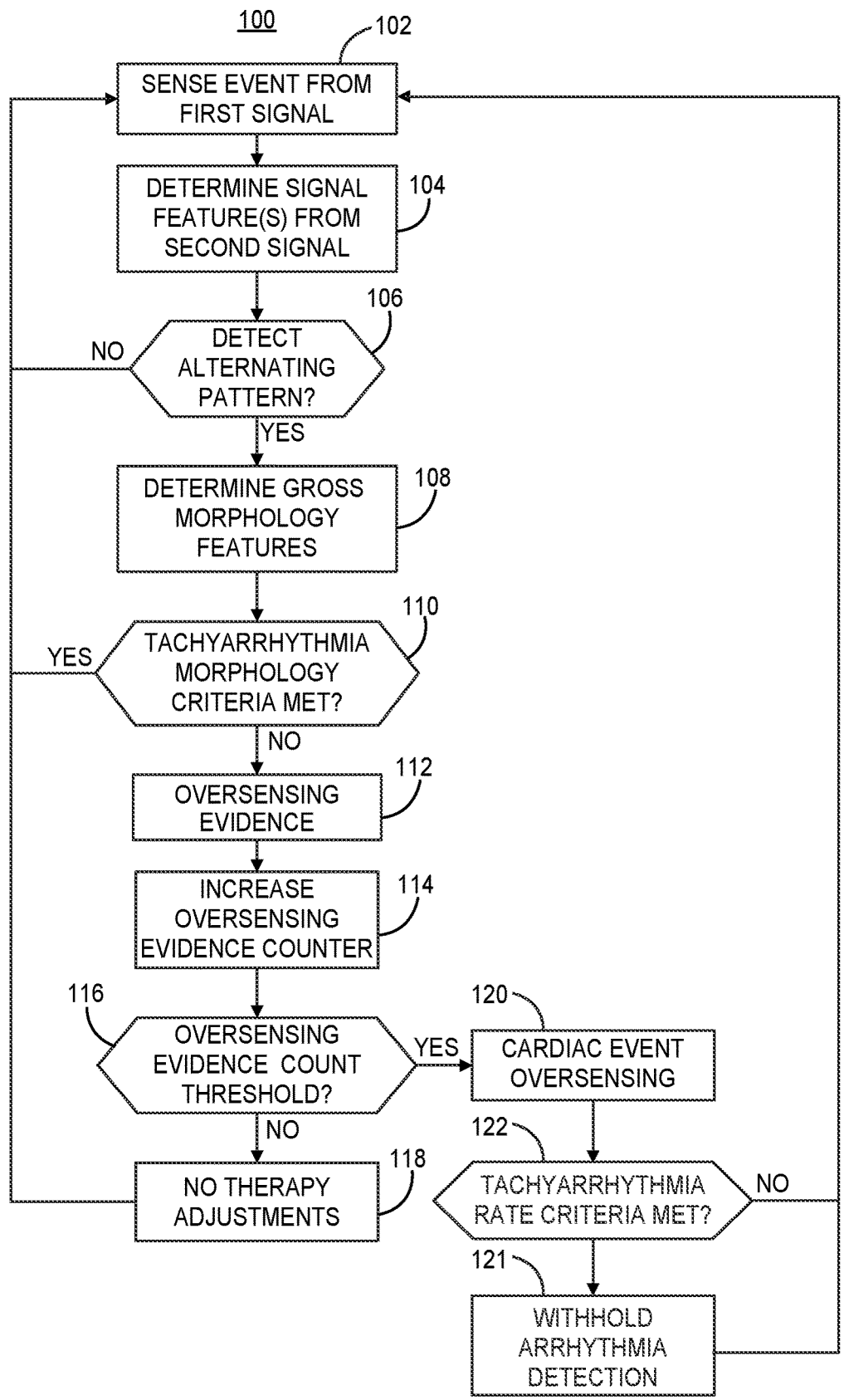
FIG. 5 is a flow chart of a method for detecting cardiac event oversensing according to one example.

FIG. 5 is a flow chart 100 of a method for detecting cardiac event oversensing according to one example. In various examples presented herein, the cardiac event oversensing being detected is PWOS, when R-waves are being intentionally sensed by the first sensing channel 83 based on an R-wave sensing threshold crossing. PWOS occurs when a P-wave of the cardiac electrical signal crosses the R-wave sensing threshold, causing the first sensing channel 83 to produce a false R-wave sensed event signal that is passed to control circuit 80. It is to be understood, however, that the techniques for detecting cardiac event oversensing may be applied for detecting R-wave oversensing when P-waves are being intentionally sensed by a sensing circuit of a medical device. In this case, R-wave oversensing occurs when an R-wave of the cardiac electrical signal crosses the P-wave sensing threshold, causing the sensing circuit to produce a false P-wave sensed event signal.

At block 102, sensing circuit 86 senses cardiac events based on cardiac event sensing threshold crossings by a first cardiac electrical signal. The cardiac electrical signal may be a relatively near field signal for increasing the likelihood of sensing cardiac events in a desired heart chamber, e.g., ventricular or atrial, without oversensing a cardiac event in the adjacent heart chamber, e.g., atrial or ventricular. In one example, cardiac events sensed at block 102 are intended to be R-waves sensed based on an R-wave sensing threshold crossing detected by the first sensing channel 83 of sensing circuit 86 as described above.

At block 104, control circuit 80 may determine one or more signal features from a cardiac electrical signal segment corresponding in time to a sensed event signal produced by the first sensing channel 83. The signal features may be determined from the second cardiac electrical signal sensed via a sensing electrode vector that is different than the sensing electrode vector used to sense the first cardiac electrical signal, from which the cardiac events are being sensed. The second cardiac electrical signal may be a relatively far field or more global cardiac signal compared to the first cardiac electrical signal and/or filtered or processed differently to enhance the specificity and sensitivity of the morphological analysis for detecting alternating signal features and tachyarrhythmia morphology signal segments. For example, the second cardiac electrical signal may be sensed using a sensing electrode vector having an interelectrode distance that is greater than the interelectrode distance of the first sensing electrode vector. Additionally or alternatively, the second cardiac electrical signal segment may be filtered by a relatively wider band pass to retain features of the cardiac electrical signal waveforms and, in some examples, filtered by a notch filter for attenuating 50-60 Hz noise. In other examples, the first cardiac electrical signal and the second cardiac electrical signal are received by the same sensing electrode vector but processed differently, e.g., filtered differently, to produce a first cardiac electrical signal that is different than the second cardiac electrical signal.

At block 104, a segment of the second cardiac electrical signal over a predetermined time interval may be buffered in memory 82. The predetermined time interval encompasses a time point at which a cardiac event was sensed from the first cardiac electrical signal. For example, in response to each R-wave sensed event signal 68 received from the first sensing channel 83 (see FIG. 4), control circuit 80 may buffer a time segment of the second cardiac electrical signal 78 (and the rectified signal 79 in some examples) from the second sensing channel 85 in memory 82. The time segment may extend from a time point earlier than the time of the R-wave sensing threshold crossing to a time point later than the R-wave sensing threshold crossing that caused the first sensing channel 83 to generate an R-wave sensed event signal 68. The time segment may be 300 to 500 ms in duration, e.g., 360 ms in duration, including sample points preceding and following the R-wave sensed event signal. For instance, as described in conjunction with FIG. 6B, a 360 ms segment may include 92 sample points when the sampling rate is 256 Hz with 24 of the sample points occurring after the R-wave sensed event signal that triggered the storage of the signal segment and 68 sample points extending from the R-wave sensed event signal earlier in time from the R-wave sensed event signal.

One or more signal features may be determined from each second cardiac electrical signal segment by control circuit 80. In one example, at least a maximum peak-to-peak amplitude occurring during the time segment of the second cardiac electrical signal is determined. The maximum peak-to-peak amplitude may be determined over the time segment of the second cardiac electrical signal as the absolute difference between a minimum sample point amplitude and a maximum sample point amplitude. As such, control circuit 80 may include a peak detector that holds the values of a minimum peak and a maximum peak detected in a comparative analysis of sample point amplitudes of the digitized, notch-filtered cardiac signal. In this example of determining a maximum peak-to-peak amplitude, the cardiac electrical signal segment is a non-rectified signal. In other examples, a rectified signal may be used and a maximum peak amplitude may be determined. A series of maximum peak-to-peak amplitudes, e.g., at least three to twelve maximum peak-to-peak amplitudes determined from a corresponding number of buffered second cardiac electrical signal segments may be stored in memory 82 so that they are available for analysis for cardiac event oversensing detection.

In other examples, the polarity (positive or negative) of the maximum absolute peak amplitude may be determined among the one or more signal features determined from each second cardiac electrical signal segment at block 104. In still other examples, a signal feature determined at block 104 may be a maximum slope, total area (e.g., integral or summation of the sample point amplitudes), or other feature of the second cardiac electrical signal that is expected to alternate when the sensed event signals produced by the first sensing channel correspond to an alternating pattern of R-waves and P-waves (e.g., P-R-P or R-P-R). Two or more signal features may be determined from each segment to detect an alternating pattern of the combination of two or more signal features in some examples.

At block 106, control circuit 80 compares consecutively determined signal features and/or event intervals to each other to criteria for detecting an alternating pattern of signal features. For example, an alternating pattern of relatively high and relatively low maximum peak-to-peak amplitudes of the second cardiac electrical signal segments may be detected at block 106. In other examples, an alternating pattern of event signal polarity may be detected at block 106. In still other examples, event time intervals may be determined between consecutively sensed event signals produced by the first sensing channel to detect an alternating pattern of long and short event intervals. The alternating pattern detected at block 106 may be one pair of high and low maximum peak-to-peak amplitudes (e.g., high-low or low-high), one pair of positive and negative event polarities (e.g., positive-negative or negative-positive), and/or one pair of long and short event intervals (e.g., long-short or short-long), occurring in either order. In other examples, an alternating pattern of at least three consecutive event signal features is required to detect the alternating pattern at block 106. Using the example of maximum peak-to-peak amplitude, a relative peak-to-peak amplitude pattern of high-low-high or low-high-low may be detected as an alternating pattern at block 106. Methods and criteria for detecting alternating patterns of relatively high and low maximum peak-to-peak amplitude differences and relatively long and short intervals are described below in conjunction with FIG. 6A.

When an alternating pattern is not detected ("no" branch of block 106), no further signal analysis may be performed by control circuit 80 for detecting cardiac event oversensing. The process may return to block 102 to continue sensing cardiac events. In response to detecting an alternating pattern of at least one signal feature ("yes" branch of block 106), e.g., alternating maximum peak-to-peak amplitude, from consecutive second cardiac electrical signal segments, control circuit 80 may determine a gross morphology feature at block 108 from one or more of the second cardiac electrical signal segments corresponding to the alternating signal feature pattern.

In some examples, when the alternating signal feature pattern suggests that the middle cardiac electrical signal segment out of three consecutive segments is an oversensed event, e.g., based on a high-low-high maximum peak-to-peak amplitude, control circuit 80 may identify the first and third segments of the cardiac electrical signal as corresponding to suspected true sensed cardiac events. The gross morphology features may be determined from the first and third segments identified as suspected true sensed cardiac events (e.g., true sensed R-waves). When the alternating pattern suggests that the first and third segments of the second cardiac electrical signal are oversensed events, e.g., based on a low-high-low maximum peak-to-peak amplitude, the gross morphology feature may be determined from the middle (second) segment of the three consecutive segments. In this case, the middle segment is identified as a second cardiac electrical signal segment corresponding to a suspected true sensed event. The gross morphology feature(s) for only the signal segments suspected to be true sensed R-waves may be compared to tachyarrhythmia morphology criteria at block 110 in some examples. In other examples, the gross morphology feature(s) may be determined from all of the segments analyzed at block 106 determined to present the alternating feature pattern and compared to tachyarrhythmia morphology criteria at block 110.

Each gross morphology feature is determined from an analysis of the sample points spanning the second cardiac electrical signal segment. The gross morphology features determined at block 108 may include an amplitude morphology metric and/or a signal width morphology metric, as examples. Gross morphology features that may be used for detecting a tachyarrhythmia morphology may include a maximum slope, a number of peaks, a total signal area, a pulse count, a low slope content, a normalized mean rectified amplitude or other morphology features. Examples of gross morphology features may include any signal feature or metric correlated to a tachyarrhythmia waveform. Example methods for determining the gross morphology features at block 108 are described below in conjunction with FIGS. 7 and 8.

At block 110, the gross morphology feature(s) may be compared to tachyarrhythmia morphology criteria. When a gross morphology feature meets tachyarrhythmia morphology criteria, cardiac event oversensing is not detected. As further described below, the tachyarrhythmia morphology criteria may require that at least one of the amplitude morphology metric or the signal width morphology metric is greater than a respective threshold as evidence of the morphology of a tachyarrhythmia waveform. When the gross morphology features do not meet tachyarrhythmia morphology criteria at block 110 ("no" branch), cardiac event oversensing evidence is detected at block 112. This detection at block 112 indicates that at least one of the second cardiac electrical signal segments corresponds to an oversensed cardiac event. When the gross morphology features do not meet criteria for detecting a tachyarrhythmia morphology at block 110, e.g., for at least one cardiac electrical signal segment identified as a suspected true sensed cardiac event, the suspected true sensed cardiac event is verified. This verification of the true sensed cardiac event in the absence of evidence of a tachyarrhythmia morphology ("no" branch of block 110), and the detection of an alternating signal feature pattern, results in an oversensing evidence detection at block 112.

Conversely, when the gross morphology feature of at least one second cardiac electrical signal segment, which may be identified as a suspected true sensed cardiac event in the alternating signal feature pattern, is determined to meet tachyarrhythmia morphology criteria, the suspected true sensed cardiac event is not verified and oversensing evidence is not detected ("yes" branch of block 110). As described below in conjunction with FIGS. 7 and 8, the gross morphology features determined at block 108 may be compared to criteria at block 110 that distinguish between a likely tachyarrhythmia morphology and a likely true cardiac event signal morphology such as a true R-wave. The process returns to block 102 to continue sensing cardiac events from the first cardiac electrical signal and monitoring for cardiac event oversensing as needed.

Control circuit 80 may include a counter or buffer that tracks the number of times evidence of oversensing is detected at block 112 out of a specified number of recent sensed cardiac events. At block 114, a counter may be increased or a flag may be set indicating the oversensing evidence detection made at block 112. For instance, a first-in-first-out buffer may store a specified number of flags. When an alternating pattern is detected and tachyarrhythmia morphology criteria are not met, a flag may be set high (e.g., to 1) to indicate oversensing evidence is detected. When an alternating pattern is not detected, or tachyarrhythmia morphology criteria are met, the flag may be set low (e/g/. to 0) to indicate oversensing evidence is not detected. The first-in-first-out buffer may update on a beat-by beat basis in some examples, as oversensing evidence is detected (or not) with the oldest flag value being discarded. The buffer may store a predetermined number of flags, e.g., up to 32 (or more) corresponding to up to 32 (or more) consecutively sensed cardiac events. The oversensing evidence detection made at block 112 indicates that at least one of the second cardiac electrical signal segments of the alternating feature pattern corresponds to a suspected oversensed event, e.g., an oversensed P-wave falsely sensed as an R-wave.

At block 116, the number of oversensing evidence detections counted (or number of oversensing evidence flags set in a buffer storing a specified number of flags in a first-in-first out basis) may be compared to an oversensing detection threshold. For example, if oversensing evidence is detected X times during a series of Y sensed cardiac event signals sensed from the first cardiac electrical signal, cardiac event oversensing is detected at block 120. In one example, if more than a threshold percentage (e.g., 20% 25%, 30%, 35%, 40% or other percentage) of sensed event signals received from the first sensing channel 83 result in an oversensing evidence detection based on the analysis of multiple, consecutive second cardiac electrical signal segments, oversensing is detected at block 120. For instance, if 3 oversensing evidence detections occur over 12 consecutive R-wave sensed event signals, or if 4 oversensing evidence detections occur over 16 consecutive R-wave sensed event signals or 8 oversensing evidence detections occur over 32 R-wave sensed event signals, cardiac event oversensing is detected at block 120. In these examples, each oversensing evidence detection may be based on an analysis of three consecutive segments of the second cardiac electrical signal.

When the threshold for detecting cardiac event oversensing is not reached at block 116, the process may return to block 102 without any therapy delivery adjustments being made by the therapy delivery circuit at block 118. When cardiac event oversensing is detected at block 120, control circuit 80 may withhold an arrhythmia detection at block 122. Control circuit 80 may, in some instances, cause therapy delivery circuit 80 to withhold an arrhythmia therapy at block 122 in response to the cardiac event oversensing detection. For example, scheduling of a cardiac electrical stimulation therapy may be withheld in response to detecting the cardiac event oversensing. As described below in conjunction with FIG. 9, when other tachyarrhythmia detection criteria are met at block 121, e.g., based on the sensed cardiac event rate or a threshold number of RRIs being less than a tachyarrhythmia detection interval at block 121, the tachyarrhythmia detection may be withheld at block 122 in response to detecting cardiac event oversensing.

In other examples, consecutively determined RRIs may be buffered in memory 82 on a first-in-first-out basis so that a specified number of RRIs are stored. When all slots of the buffer are filled with an RRI value, each RRI that is less than a tachyarrhythmia detection interval may be counted as a tachyarrhythmia interval. Control circuit 80 may determine that tachyarrhythmia rate criteria are met at block 121 when a threshold number of tachyarrhythmia intervals are counted in the buffer. However, an RRI that is less than a tachyarrhythmia detection interval corresponds in time to a flag set in response to detecting cardiac event oversensing, the RRI may be ignored and not counted toward reaching the threshold number of tachyarrhythmia detection intervals. In this way, arrhythmia detection may be withheld by ignoring RRIs that coincide with cardiac oversensing detections.

An anti-tachyarrhythmia therapy, e.g., ATP and/or CV/DF shock(s) may be withheld by rejecting or withholding the tachyarrhythmia detection at block 122 to avoid delivering an inappropriate therapy due to cardiac event oversensing. In this way, the performance of the medical device for detecting and treating tachyarrhythmias is improved by detecting cardiac event oversensing and avoiding an inappropriate or unnecessary therapeutic response of the medical device due to cardiac event oversensing.

Figure 6A:
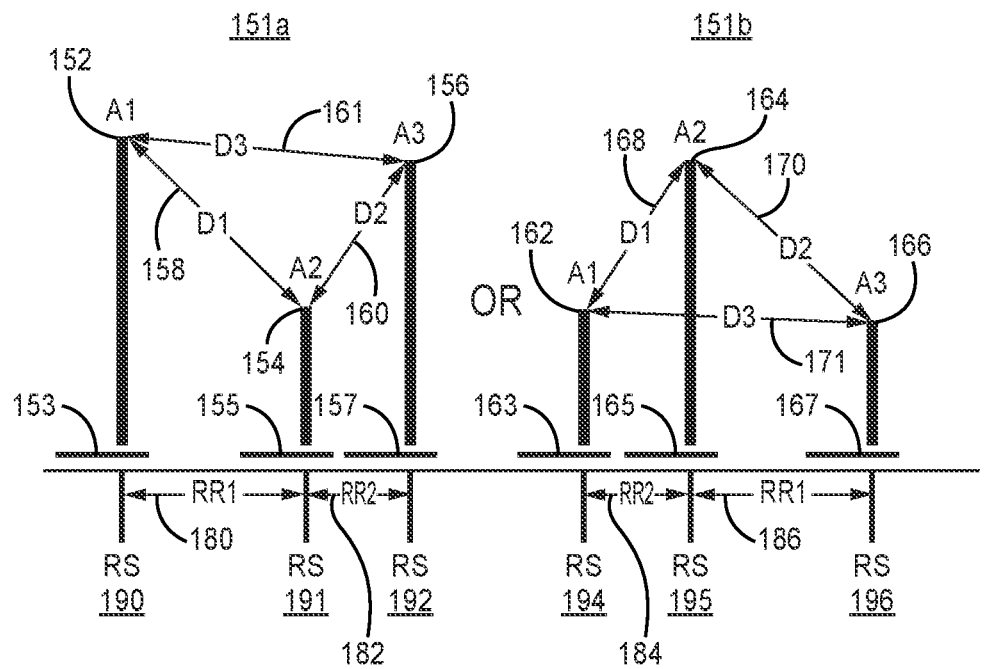
FIG. 6A is a conceptual diagram of a method for detecting an alternating pattern of cardiac signal features according to one example.

FIG. 6A is a conceptual diagram 150 of a method for detecting an alternating pattern of cardiac signal features according to one example. Two examples 151a and 151b are depicted in which an alternating high-low-high maximum peak-to-peak amplitude pattern is detected in example 151a, and an alternating low-high-low maximum peak-to-peak amplitude pattern is detected in example 151b. In these examples 151a and 151b, the first sensing channel 83 is configured to sense R-waves based on R-wave sensing threshold crossings by the first cardiac electrical signal. In response to each R-wave sensing threshold crossing, an R-wave sensed event signal 190, 191, 192, 194, 195, and 196 is produced by the sensing circuit 86. In the separate examples 151a and 151b, R-wave sensed event signals 190, 191 and 192 are three consecutive R-wave sensed event signals, and R-wave sensed event signals 194, 195 and 196 are three consecutive R-wave sensed event signals. Each R-wave sensed event signal 190-196, triggers the storage of a segment of the second cardiac electrical signal 78 (see FIG. 4) produced by the second sensing channel 85 over a respective time interval 153, 155, 157, 163, 165, and 167, with each individual time interval encompassing a time point at which the triggering R-wave sensed event signal (190, 191, 192, 194, 195, and 196) occurred. The second cardiac electrical signal may be buffered in memory 82 as it is sensed such that a signal segment may be stored over each time interval 153, 155, 157, 163, 165 and 167 that starts earlier than the respective triggering R-wave sensed event signal and ends after the triggering R-wave sensed event signal.

Figure 6B:
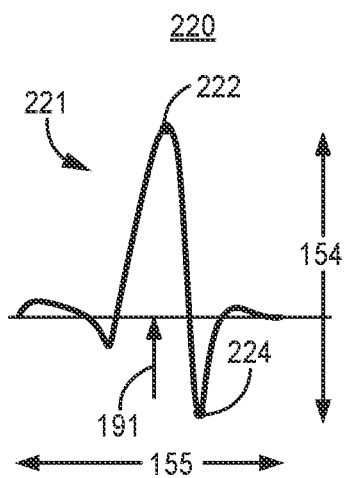
FIG. 6B is an illustration of a cardiac electrical signal segment stored over a time interval in response to an R-wave sensed event signal.

FIG. 6B is an illustration 220 of the second cardiac electrical signal segment 221 stored over time interval 155 in response to the R-wave sensed event signal 191 (corresponding to identically number time interval 155 and R-wave sensed event signal 191 shown in FIG. 6A). Time segment 155 begins after the preceding R-wave sensed event signal 190 and ends prior to the next R-wave sensed event signal 192. The second cardiac electrical signal (from sensing channel 85) may be buffered in memory 82 at a desired sampling rate, e.g., 128 Hz or 256 Hz, until an R-wave sensed event signal 191 is received at which point the desired number of sample points preceding the R-wave sensed event signal 191, e.g., 68 sample points when the sampling rate is 256 Hz, and the desired number of sample points following the R-wave sensed event signal 191, e.g., 24 of the sample points occurring after the R-wave sensed event signal 191, are stored in memory 82, in a designated buffer, as a second cardiac electrical signal segment 221. In other examples, a higher or lower sampling rate may be used, e.g., a sampling rate of 512 Hz or 128 Hz. A correspondingly higher or lower number of sample points may be used to analyze the cardiac signal segment over the same or similar time interval extending before and after the time point that the R-wave was sensed. Time interval 155 over which second cardiac electrical signal segment 221 is stored for analysis may be between 100 ms and 500 ms in length in various examples and is 360 ms in one example. Sample points of the second cardiac electrical signal that are buffered before the start of the time segment 155 and after preceding time segment 153, may be discarded.

In some examples, the second cardiac electrical signal segment 221 is a non-rectified signal such that a maximum peak-to-peak amplitude 154 may be determined as the absolute difference between the maximum sample point amplitude 222 and the minimum sample point amplitude 224 detected over the signal segment 155. In other examples, a maximum peak, minimum peak or a maximum peak of the rectified signal may be determined. In the example shown, control circuit 80 determines a maximum peak-to-peak amplitude of the second cardiac electrical signal during each of the time segments 153, 155, 157, 163, 165 and 167. For example, the maximum peak-to-peak amplitude A2 154 is determined from the second cardiac electrical signal segment 221 stored over time segment 155 as the absolute difference between the maximum peak sample point amplitude 222 and the minimum peak sample point amplitude 224. Referring again to FIG. 6A, the maximum peak amplitude A1 152 is determined from the second cardiac electrical signal segment stored over time segment 153; the maximum peak-to-peak amplitude A3 156 is determined from the second cardiac electrical signal segment stored over time segment 157, and so on. The maximum and minimum sample point amplitudes used to determine the peak-to-peak amplitudes 152, 154, 156, 162, 164 and 166 may occur at any time during the respective time segment 153, 155, 157, 163, 165, and 167 and are not necessarily the amplitude at the time of the R-wave sensed event signals 190, 191, 192, 194, 195 and 196.

Once three consecutive maximum peak-to-peak amplitudes are determined from three consecutively stored second cardiac electrical signal segments, the differences between consecutive maximum peak-to-peak amplitudes are determined. In example 151a, the first amplitude difference D1 158 is determined between amplitude A1 152 and amplitude A2 154. A second amplitude difference D2 160 is determined between the second amplitude A2 154 and the third amplitude A3 156. The first and second amplitude differences 158 and 160 between the three consecutively determined maximum peak-to-peak amplitudes 152, 154 and 156 may be compared to difference thresholds to detect an alternating pattern of maximum peak-to-peak amplitude in the second cardiac electrical signal segments.

The difference threshold may be a fixed value or set based on at least one of the determined maximum peak-to-peak amplitudes of the three consecutively determined peak-to-peak amplitudes 152, 154 and 156. In some examples, the larger peak-to-peak amplitude of the two amplitudes being compared is identified, and the difference threshold is set to a percentage of the larger of the two amplitudes. For instance, in the first example 151a, the absolute value of the first difference D1 158 is compared to a percentage of the first, larger maximum peak-to-peak amplitude A1 152. The second difference D2 160 is compared to a percentage of the third (larger) maximum peak-to-peak amplitude A3 156. The percentage of the maximum peak-to-peak amplitude used for setting a difference threshold may be 15 to 30%, as examples, and is 22% in one example. When the absolute value of difference D1 158 is greater than 22% of peak-to-peak amplitude A1 152 and difference D2 160 is greater than 22% of peak-to-peak amplitude A3 156, an alternating pattern of high-low-high is detected by control circuit 80. The R-wave sensed event signal 191 corresponding to the low maximum peak-to-peak amplitude A2 154 in the detected high-low-high pattern is a suspected oversensed P-wave. The R-wave sensed event signals 190 and 192, corresponding to high maximum peak-to-peak amplitudes 152 and 156 in the second cardiac electrical signal segments stored over time intervals 153 and 157, respectively, may be identified as suspected true sensed R-waves. Control circuit 80 may increase an oversensed cardiac event evidence counter or set an oversensed cardiac evidence flag to track the number of times a pattern of cardiac event oversensing is identified over three consecutive R-wave sensed event signals.

In addition to detecting the high-low-high peak-to-peak amplitude pattern, control circuit 80 may verify stability in the alternating high peak-to-peak amplitudes A1 152 and A3 156. These first and third amplitudes 152 and 156, which may correspond to true sensed R-waves, may be required to be within a stability threshold of each other. In one example, the difference D3 161 between peak-to-peak amplitude A1 152 and peak-to-peak amplitude A3 156 may be required to be less than a threshold percentage, e.g., less than 50%, of the highest maximum peak-to-peak amplitude (A1 152 in this example) out of the three signal segments. The requirement of D3 being less than a stability threshold, which may be set based on the highest maximum peak-to-peak amplitude, requires the maximum peak-to-peak amplitudes A1 152 and A3 156 of the signal segments corresponding to the two suspected true R-wave sensed event signals 190 and 192 to be stable.

The comparisons of signal amplitude differences for detecting high-low-high or low-high-low patterns may be performed using the maximum peak amplitude of R-waves sensed from the first sensing channel in some examples. The first and second differences between three consecutively sensed R-waves of the first cardiac electrical signal may be compared to respective thresholds, which may be different than the thresholds applied to the maximum peak-to-peak amplitude differences determined from the second cardiac electrical signal segments. In one example, the difference between first and second sensed R-wave amplitudes is required to be greater than 20% (or other percentage) of the largest one of the first and second sensed R-wave amplitudes. Additionally or alternatively, the difference between first and second maximum peak amplitudes determined from the second cardiac electrical signal is required to be greater than 20% of the highest one of the first and second maximum peak amplitudes or multiple thereof, e.g., 20% of 1.5 times the highest maximum peak amplitude.

In other examples, additional criteria may be applied before counting the detected alternating pattern of signal features as a detection of PWOS evidence. For example, a polarity (positive or negative) of the maximum peak amplitude of the non-rectified signal may be determined for each of the second cardiac electrical signal segments or at least the segment(s) suspected of being an oversensed event. In other examples, the RR intervals 180 and 182 between the consecutive R-wave sensed event signals 190 and 191 and the consecutive R-wave sensed event signals 191 and 192, respectively, may be compared to alternating pattern detection criteria at block 106 of FIG. 5.

For instance, the sum of RR interval 180 and RR interval 182 may be required to fall within a threshold range, e.g., greater than 380 ms or other fast interval threshold and less than 1200 ms or other slow interval threshold. The threshold range may correspond to an expected range of true, non-tachyarrhythmia RR intervals. When at least one of the three consecutive R-wave sensed event signals 190, 191 or 192 is an oversensed P-wave, the sum of the two RR intervals 180 and 182 may represent a true RR interval. Thus their sum should fall within an expected RR interval range.

The RR intervals 180 and 182 may additionally or alternatively be compared to each other or their difference may be compared to a difference threshold to verify that a likely long-short pattern exists corresponding to an R-P-R pattern of the R-wave sensed event signals 190, 191 and 192. In some examples, when one RR interval 180 or 182 is shorter than a threshold percentage (e.g., less than 60%, 50%, 40% or other percentage) than the other RR interval 182 or 180 a short-long or long-short pattern is detected. Additionally or alternatively, at least one of the two consecutive RR intervals may be required to be less than a threshold interval, e.g., less than a threshold interval of 360 to 400 ms. In some instances, the threshold interval is set to a tachyarrhythmia detection interval plus an offset, e.g., 40 ms longer than a VT or VF detection interval. This short interval in combination with an alternating amplitude pattern may be evidence of PWOS.

These examples of comparative analysis of RR intervals may be performed on RR intervals determined between consecutive R-wave sensed event signals produced by the first sensing channel 83. Additionally or alternatively, any or all of these examples of comparative analysis of RR intervals may be performed by determining RR intervals between maximum peak amplitudes or R-wave sensing threshold amplitude crossings of the second cardiac electrical signal. The determination of a long-short RR interval pattern in combination with a high-low-high amplitude pattern may result in detection of PWOS evidence by control circuit 80. As described below, tachyarrhythmia morphology criteria may be applied to one or more of the second cardiac electrical signal segments presenting the alternating signal feature pattern before detecting the alternating pattern as evidence of PWOS.

In the second example 151b, control circuit 80 is configured to detect the low-high-low pattern of the maximum peak-to-peak amplitudes of the second cardiac electrical signal buffered over time segments 163, 165 and 167, triggered by respective R-wave sensed event signals 194, 195 and 196. In this case, the first amplitude difference D1 168 is determined between the first maximum peak-to-peak amplitude A1 162 and the second maximum peak-to-peak amplitude A2 164 (e.g., A1 minus A2). The second amplitude difference D2 170 is determined between the second maximum peak-to-peak amplitude A2 164 and the third maximum peak-to-peak amplitude A3 166 (e.g., A2 minus A3). The absolute value of D1 168 may be compared to a difference threshold set based on one of the amplitudes A1 162, A2 164, or A3 166, e.g., to a percentage of the higher, second maximum peak-to-peak amplitude A2 164. In one example, the difference threshold is set to 22% of A2 164 (the greater of A1 and A2). The second amplitude difference D2 170 may also be compared to a difference threshold set to a percentage of the higher second maximum peak-to-peak amplitude A2 164. When the first amplitude difference D1 168 and the second amplitude difference D2 170 are both greater than a percentage of the second maximum peak amplitude A2 164, the low-high-low maximum peak-to-peak amplitude pattern is detected by control circuit 80.

In addition to detecting the low-high-low peak-to-peak amplitude pattern, control circuit 80 may verify stability in the alternating low peak-to-peak amplitudes A1 162 and A3 166. These first and third amplitudes 162 and 166, which may correspond to oversensed P-waves, may be required to be within a stability threshold of each other. In one example, the difference D3 171 between A1 162 and A3 166 may be required to be less than a threshold percentage, e.g., less than 50%, of the maximum of these two low peak-to-peak amplitudes (A1 162 in this example). The requirement of D3 being less than a stability threshold, e.g., set based on the higher peak-to-peak amplitude of the alternating low peak-to-peak amplitudes A1 162 and A3 166, requires the peakto-peak amplitudes of the second cardiac electrical signal segments corresponding to the two suspected oversensed P-waves to be stable.

Accordingly, once a low-high-low or a high-low-high peak-to-peak amplitude pattern is detected based on consecutive peak-to-peak amplitude differences being greater than a difference threshold, the difference between the first and third peak-to-peak amplitudes may be required to be less than a stability threshold for the three consecutive signal segments to be detected as an alternating pattern of signal features. The difference threshold may be set to a percentage of the highest maximum peak-to-peak amplitude out of all three consecutive signal segments or out of the two signal segments being compared. The stability threshold may be set to a percentage of the higher of the first and third peak-to-peak amplitudes. It is to be understood that, in other examples, the difference and stability thresholds may be defined differently than the specific examples give here. For example, the difference and stability thresholds for detecting an alternating signal feature pattern may be based on a percentage of a lower one of the maximum peak-to-peak amplitudes instead of the highest maximum peak-to-peak amplitude or based on a mean or median peak-to-peak amplitude of all segments or only segments correspond to suspected true R-waves, to a predetermined threshold value, etc.

As described above, additional criteria, such as the polarity of the maximum peak amplitude(s) of first and third time segments 163 and 165 and/or second time segment 165 may be compared to polarity criteria for detecting PWOS evidence. In other examples, the consecutive RR intervals 184 and 186 may be compared to each other or their difference may be compared to an RR interval difference threshold to verify that a short-long pattern of RRIs is detected to support the detection of the low-high-low maximum peak-to-peak amplitude pattern that suggests the first and third R-wave sensed event signals 194 and 196 are suspected oversensed P-waves and the second, middle R-wave sensed event signal 195 is a suspected true R-wave. In response to detecting the low-high-low pattern, an oversensing evidence counter may be increased or an oversensing evidence flag may be set to track the number of times an alternating pattern of consecutively determined second cardiac electrical signal features is detected.

Even though two likely P-waves may be oversensed in the series of the three R-wave sensed event signals 194, 195 and 196, the oversensing evidence counter may be increased by one or a single flag may be set. In some examples, overlapping, moving sets of three second cardiac electrical signal segments may be evaluated for detecting alternating signal feature patterns. For instance, the third R-wave sensed event signal 196 may become the second R-wave sensed event signal of the next set of three consecutive R-wave sensed event signals, which may also meet the oversensing evidence criteria (in a high-low-high pattern). When a moving set of three (or other selected number of) consecutively determined maximum peak-to-peak amplitudes (or other signal feature) is used to detect the alternating signal feature pattern, the oversensing evidence counter may be increased once (or a single oversensing evidence flag set) in response to each detection of an alternating signal feature pattern. An oversensing detection threshold set to X detections of oversensing evidence out of Y consecutively sensed events may take into account the possible double counting of some suspected oversensed events in the detected alternating patterns.

In other examples, consecutive sets of second cardiac electrical signal segments may be non-overlapping. For instance, three signal segments corresponding to three consecutive R-wave sensed event signals may be analyzed then control circuit 80 may wait for the next three R-wave sensed event signals to analyze the next three, non-overlapping segments of the second cardiac electrical signal. An oversensing evidence counter may be increased by one for each set of signal segments detected as an alternating signal feature pattern. In other examples, the oversensing evidence counter (or number of flags set) may be increased by the number of suspected oversensed cardiac events in each detected alternating signal feature pattern, e.g., by one in example 151a and by two in example of 151b.

Figure 7:
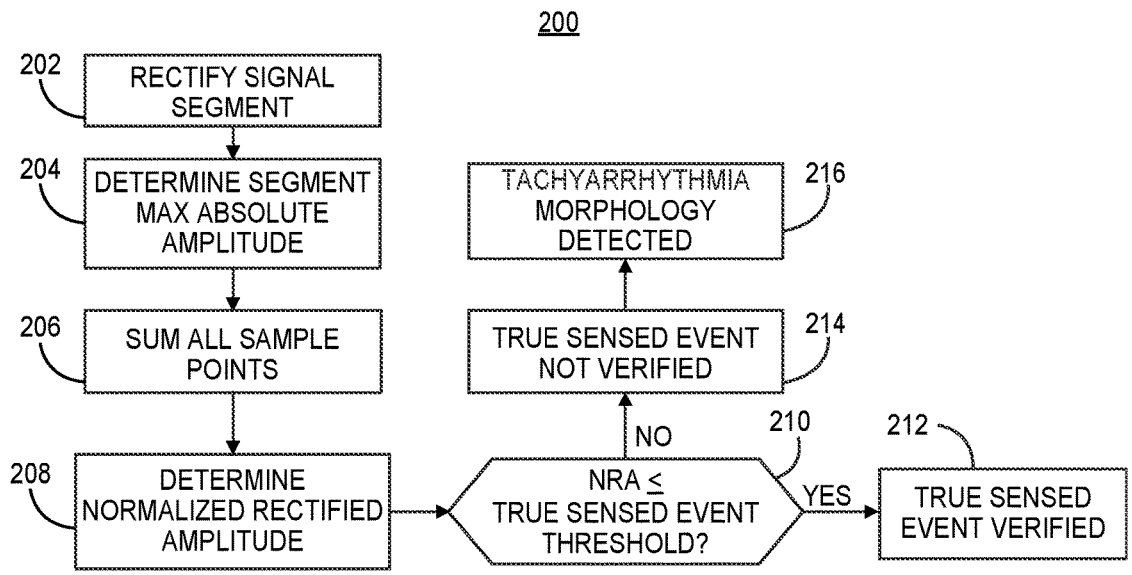
FIG. 7 is a flow chart of a method for determining a gross morphology metric for verifying a suspected true sensed cardiac event in an alternating signal feature pattern of cardiac electrical signal segments according to one example.

FIG. 7 is a flow chart 200 of a method for determining a gross morphology metric for verifying a suspected true sensed cardiac event in an alternating signal feature pattern of cardiac electrical signal segments according to one example. Each cardiac electrical signal segment analyzed for determining a gross morphology metric may be buffered as generally described in conjunction with FIG. 6B. The method of flow chart 200 may generally be performed at blocks 108 and 110 of FIG. 5 to analyze at least one second cardiac electrical signal segment out of a consecutive series of segments presenting the alternating signal feature pattern for detecting a tachyarrhythmia morphology. For example, when three segments of the second cardiac electrical signal present an alternating pattern, the first and third segments may be analyzed to determine gross morphology metrics when the alternating pattern suggest that the second, middle segment corresponds to an oversensed P-wave and the first and third segments correspond to suspected true R-waves. When the alternating pattern suggests that the second middle segment corresponds to a suspected true sensed cardiac event and the first and third segments correspond to suspected oversensed events, the second, middle segment may be analyzed to determine gross morphology metrics. In other examples, all of the segments included in a detected alternating pattern sequence may be analyzed for determining gross morphology metrics.

The method of FIG. 7 corresponds to the analysis of one second cardiac electrical signal segment for verifying a suspected true cardiac event in an alternating signal feature pattern based on the absence of evidence of a tachyarrhythmia morphology. At block 202, the second cardiac electrical signal segments stored on a triggered basis in response to R-wave sensed event signals may be rectified. In some examples, a 360 ms segment of the notch-filtered second cardiac electrical signal may be rectified by rectifier 75 included second sensing channel 85. At block 202, the buffered, rectified signal segment may be retrieved by control circuit 80 from memory 82. In other examples, a notch-filtered signal segment may be buffered in memory 82 and control circuit 80 may perform the rectification of the stored signal segment at block 202. The rectified signal segment obtained at block 202 may correspond to a signal segment identified as a suspected true sensed cardiac event, e.g., a true sensed R-wave, based on the detected high-low-high or low-high-low alternating signal feature pattern as described above in conjunction with FIG. 6A.

Control circuit 80 determines the maximum absolute amplitude of the rectified, notch-filtered signal segment at block 204. The maximum absolute amplitude may be determined from among all sample points spanning the selected signal segment. As described above, a 360 ms segment of the second cardiac electrical signal may include 92 sample points when the sampling rate is 256 Hz, with 24 of the sample points occurring after the R-wave sensed event signal that triggered the storage of the signal segment and 68 sample points extending from the R-wave sensed event signal earlier in time from the R-wave sensed event signal. The sample point having the maximum amplitude in the rectified signal is determined at block 204.

At block 206, the amplitudes of all sample points of the rectified signal segment are summed. At block 208, the gross morphology metric of the signal segment is determined as a normalized rectified amplitude (NRA) based on the maximum absolute amplitude determined at block 204 and the summed sample point amplitudes determined at block 206. In one example, the NRA is determined as a predetermined multiple or weighting of the summation of all sample point amplitudes of the notch-filtered and rectified signal segment normalized by the maximum amplitude. For instance, the NRA may be determined as four times the summed amplitudes divided by the maximum absolute amplitude, which may be truncated to an integer value. This NRA may be determined as a gross morphology amplitude metric at block 108 of FIG. 5.

The gross morphology amplitude metric may be inversely correlated to the probability of the signal segment sample points being at a baseline amplitude during the time interval of the signal segment. The higher the gross morphology amplitude metric is, the lower the probability that the signal is at a baseline amplitude at any given time point during the time interval of the signal segment. A relatively low probability that the signal is at baseline during the time interval may be correlated to a tachyarrhythmia morphology, e.g., a ventricular fibrillation morphology, which may resemble a sinusoidal signal. When the gross morphology amplitude metric exceeds a threshold value for verifying a suspected true sensed R-wave, the more likely the second cardiac electrical signal segment has a tachyarrhythmia morphology. When the gross morphology amplitude metric is less than the threshold value, the higher the probability that the signal is at a baseline amplitude at a given time point during the time interval of the signal segment. A relatively higher probability of a signal sample point being at baseline during the time interval of the signal segment may be correlated to a true, relatively narrow R-wave signal occurring during the signal segment, with baseline amplitude portions of the signal segment occurring before and after the true R-wave.

As such, when the gross morphology amplitude metric is higher than the true sensed event threshold, evidence of a true sensed R-wave is not confirmed. In this case, the suspected true sensed event is not verified, precluding detection of oversensing evidence. At block 210, the NRA is compared to a true sensed event threshold. The true sensed event threshold for verifying a suspected true cardiac event may be set between 100 and 150, and is set to 125 in some examples, such as when 92 sample points are summed and multiplied by a weighting factor of four and normalized by the maximum absolute amplitude. The threshold applied at block 210 to discriminate between a true sensed R-wave and a tachyarrhythmia morphology in the second cardiac electrical signal segment will depend on various factors such as the amplification and number of sample points summed, the multiplication or weighting factor of the summed sample points, etc.

Control circuit 80 may verify a suspected true cardiac event of an alternating signal feature pattern at block 212 in response to the NRA being less than the true sensed event threshold. When the NRA is greater than (or equal to) the true event threshold at block 210, the suspected true sensed event is not verified at block 214. Tachyarrhythmia morphology evidence is detected at block 216. With reference to FIG. 5, evidence of oversensing is not detected ("yes" branch of block 110) in response to evidence of a tachyarrhythmia morphology based on the NRA being greater than the true sensed event threshold even though an alternating signal feature pattern may be detected.

When the gross morphology amplitude metric determined at block 108 of FIG. 5 (according to the method of FIG. 7) is greater than the true sensed event threshold at block 210, evidence of a tachyarrhythmia morphology is detected (block 110 of FIG. 5), precluding detection of oversensing evidence. When at least one (or all) second cardiac electrical signal segment(s) corresponding to a suspected true R-wave signal in the alternating pattern of signal segments is/are verified based on the gross morphology amplitude metric being less than or equal to a true sensed event threshold, control circuit 80 does not detect tachyarrhythmia morphology evidence and may detect oversensing evidence in response to the verification of the suspected true sensed event(s) and the alternating pattern of the second cardiac electrical signal segment features. In this case, tachyarrhythmia morphology evidence is not detected at block 110 of FIG. 5, leading to the detection of oversensing evidence at block 112.

Figure 8:
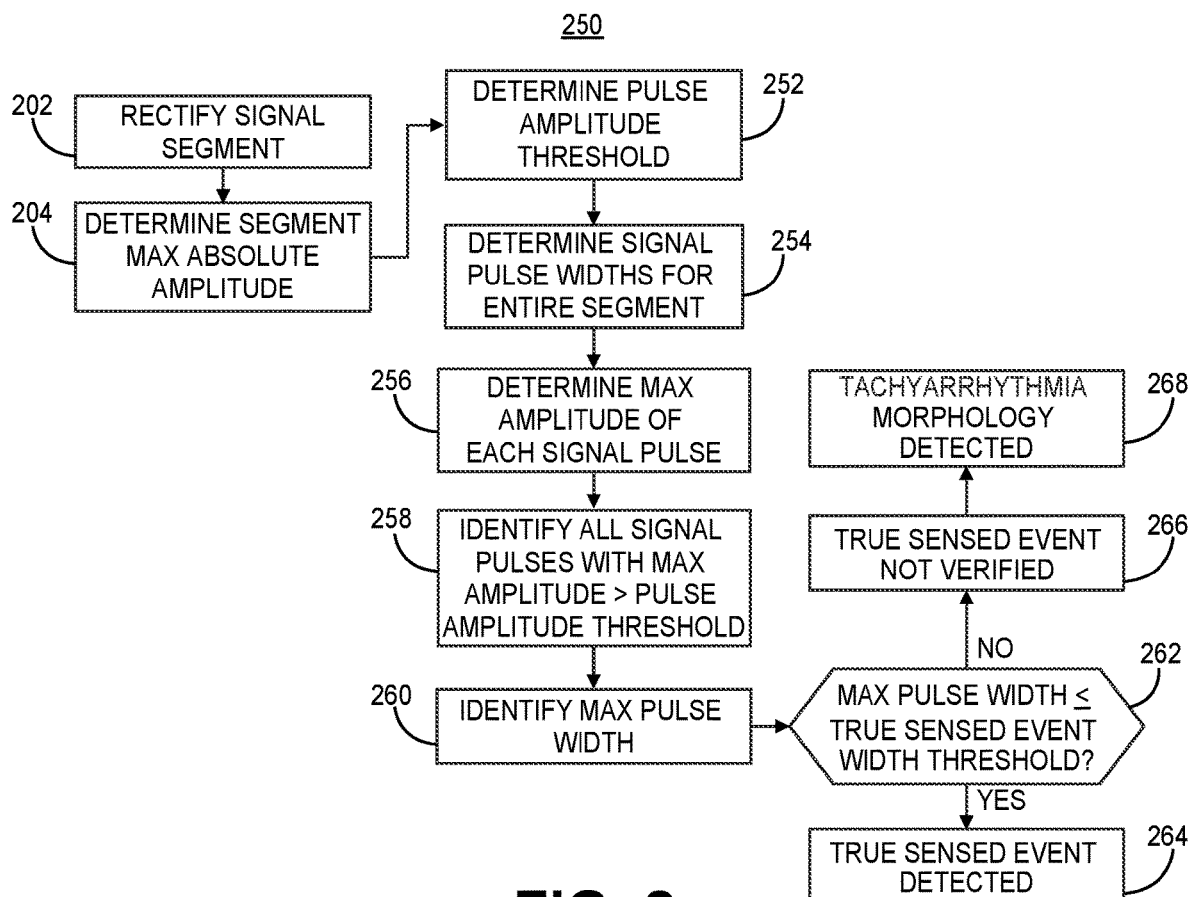
FIG. 8 is a flow chart of a method for verifying a suspected true sensed cardiac event in a cardiac electrical signal segment based on a gross morphology metric according to another example.

FIG. 8 is a flow chart 250 of a method for verifying a suspected true sensed cardiac event in a cardiac electrical signal segment based on a gross morphology metric according to another example. The process of flow chart 250 may be performed by ICD 14 for determining a gross morphology signal width metric at block 108 of FIG. 5. Blocks 202 and 204 correspond to identically-numbered blocks described above in conjunction with FIG. 7. The notch-filtered, rectified signal segment determined at block 202, which may correspond to a suspected true sensed cardiac event based on a detected alternating signal feature pattern. The notch-filtered, rectified signal segment may be used to determine a maximum absolute amplitude of the signal segment at block 204.

Control circuit 80 determines a pulse amplitude threshold at block 252 based on the maximum absolute amplitude determined at block 204. This pulse amplitude threshold may be used for identifying a signal pulse having a maximum signal width out of all signal pulses occurring during the time interval of the second cardiac electrical signal segment. For example, the pulse amplitude threshold used for determining the gross morphology signal width metric may be set to half the maximum absolute amplitude of the rectified, notch-filtered signal segment.

At block 254, control circuit 80 determines the signal width for all signal pulses of the second cardiac electrical signal segment. Each signal pulse in the signal segment may be identified by identifying two consecutive zero amplitude or baseline amplitude sample points of the rectified signal segment (or two consecutive zero crossings of a non-rectified signal segment). All signal pulses between two consecutive baseline amplitude sample points are identified at block 254. The signal pulses may be identified from the non-rectified signal segment to enable signal pulses to be identified between zero-crossings, in some examples. The signal width of each identified signal pulse is determined as the number of sample points (or corresponding time interval) between the pair of consecutive baseline amplitude sample points (or zero crossings). The absolute maximum amplitude of each rectified signal pulse is determined at block 256. All signal pulses having an absolute maximum amplitude that is greater than or equal to the pulse amplitude threshold determined at block 252 are identified at block 258. For example, all signal pulses having a maximum amplitude that is at least half the maximum absolute amplitude determined at block 204 are identified at block 258. The maximum signal pulse width is determined at block 260 by comparing the signal pulse widths of all signal pulses identified at block 258 as having a maximum amplitude that is at least the pulse amplitude threshold. The maximum pulse width identified at block 260, out of all signal pulses identified at block 258, may be determined as the gross morphology signal width metric at block 108 of FIG. 5.

The gross morphology signal width metric may be correlated to the probability of the signal segment having a tachyarrhythmia morphology. For example, a relatively high gross morphology signal width metric may be evidence of a tachyarrhythmia morphology, such as relatively wide ventricular fibrillation waves. Conversely, a relatively low gross morphology signal width metric may be evidence of a relatively narrow, true R-wave occurring during the time interval of the second cardiac electrical signal segment. A suspected true sensed R-wave may be verified by a relatively low gross morphology signal width metric, which supports detection of oversensing evidence based on a detected alternating signal feature pattern.

Control circuit 80 compares the maximum pulse width identified at block 260 to a true sensed cardiac event width threshold at block 262. In one example, the true sensed cardiac event width threshold is set to 20 sample points when the sampling rate is 256 Hz. When the maximum signal pulse width is less than the width threshold, control circuit 80 verifies the suspected true cardiac event at block 264. A maximum signal pulse width that is less than or equal to the width threshold may correspond to a true, relatively narrow R-wave, e.g., during a sinus rhythm. Verification of the suspected true sensed cardiac event may support a cardiac event oversensing detection when an alternating pattern of signal features is detected. Oversensing evidence may be detected at block 112 of FIG. 5 in response to detecting the alternating pattern at block 106 and verifying at least one suspected true cardiac sensed event based on at least the gross morphology signal width metric being less than the true sensed event width threshold.

When the maximum pulse width is greater than the width threshold at block 262, the suspected true sensed cardiac event is not verified at block 266. Instead, the relatively wide maximum signal pulse width may be detected at block 268 as evidence of a tachyarrhythmia morphology present in the segment of the second cardiac electrical signal being analyzed. Evidence of the tachyarrhythmia morphology precludes verification of a suspected true sensed cardiac event and detection of oversensing evidence at block 112 of FIG. 5, even when an alternating pattern of second cardiac electrical signal segment features has been detected.

In various examples, both the gross morphology amplitude metric and the gross morphology signal width metric may be determined (at block 110 of FIG. 5 according to the techniques of FIG. 7 and FIG. 8) and compared to true cardiac event criteria or thresholds at block 110 of FIG. 5. In some examples, both of the gross morphology amplitude metric and the gross morphology signal width metric may be required to meet the true cardiac sensed event criteria, e.g., both may be required to be less than or equal to a respective threshold value, for suspected true cardiac sensed event to be verified and allow oversensing evidence to be detected. When only one of the gross morphology amplitude or the gross morphology signal width is greater than the respective true cardiac sensed event threshold value, evidence of a tachyarrhythmia morphology is detected in the second cardiac electrical signal segment at block 110 of FIG. 5, precluding detection of oversensing evidence. In other examples, at least one of the gross morphology amplitude and signal width metrics of the suspected true sensed cardiac event signal segment(s) may be required to be less than or equal to the respective true cardiac event threshold value in order to detect oversensing evidence based on the alternating signal feature pattern.

The gross morphology amplitude metric determined by the method of FIG. 7 and the gross morphology signal width metric determined by the method of FIG. 8 may be used in combination to verify suspected true R-waves in an alternating signal feature pattern. Evidence of a tachyarrhythmia morphology based on the gross morphology metrics prevents verification of the suspected true R-waves and precludes detection of oversensing evidence, in some examples. A segment of the second cardiac electrical signal that has a relatively high gross morphology amplitude metric and/or relatively high gross morphology signal width metric is evidence of a tachyarrhythmia morphology.

Figure 9:
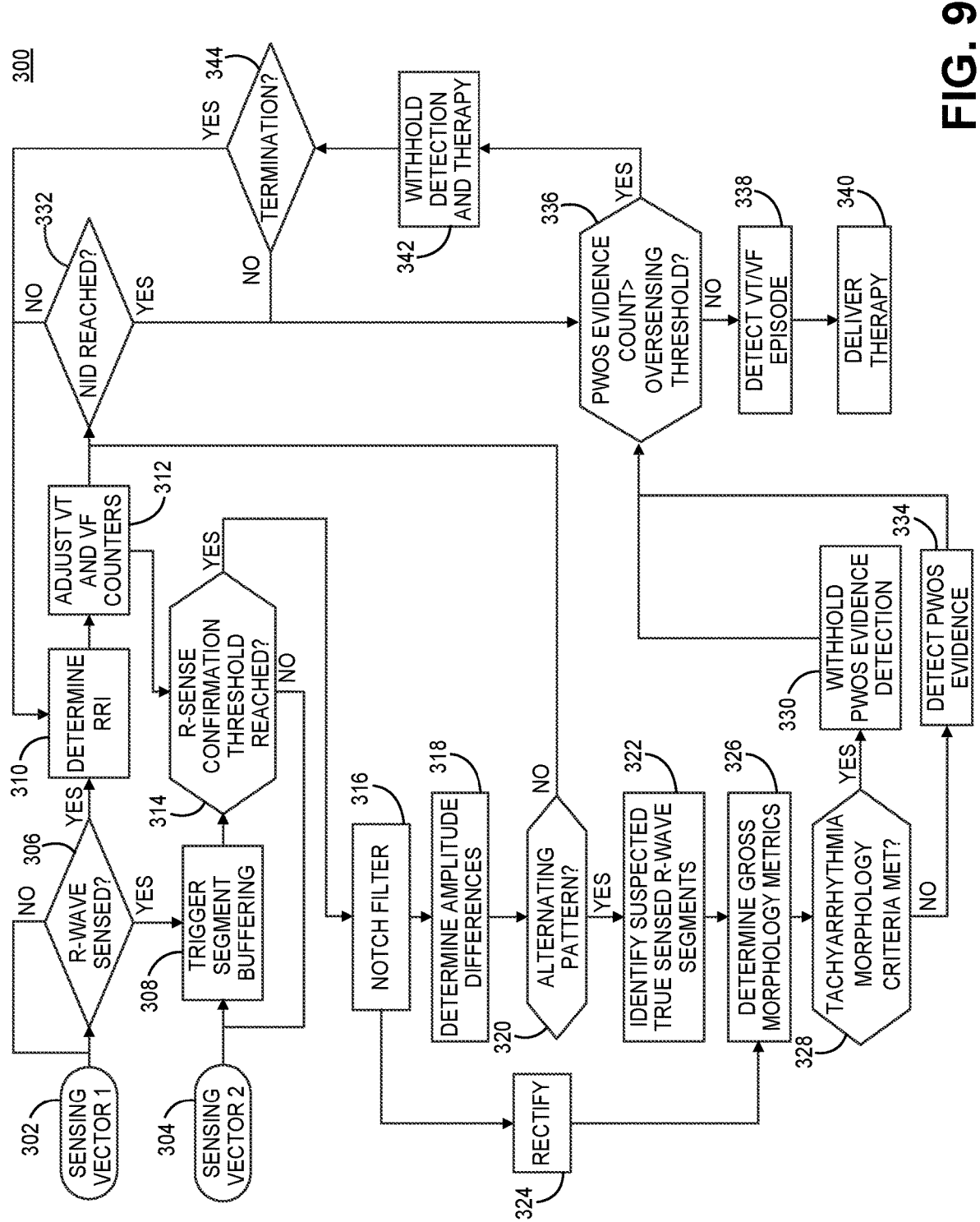
FIG. 9 is a flow chart of a method for detecting P-wave oversensing and rejecting a ventricular tachyarrhythmia detection in response to detecting P-wave oversensing according to one example.

FIG. 9 is a flow chart 300 of a method performed by ICD 14 for detecting P-wave oversensing and rejecting a ventricular tachyarrhythmia detection in response to detecting P-wave oversensing according to one example. At blocks 302 and 304, two different sensing electrode vectors may be selected by sensing circuit 86 for receiving a first cardiac electrical signal by a first sensing channel 83 and a second cardiac electrical signal by a second sensing channel 85, respectively. The two sensing electrode vectors may be selected by switching circuitry included in sensing circuit 86 under the control of control circuit 80. In some examples, the two sensing electrode vectors are programmed by a user and retrieved from memory 82 by control circuit 80 and passed to sensing circuit 86 as vector selection control signals.

The first sensing electrode vector selected at block 302 for obtaining a first cardiac electrical signal may be a relatively short bipole, e.g., between electrodes 28 and 30 or between electrodes 28 and 24 of lead 16 or other electrode combinations as described above. The relatively short bipole may include electrodes that are in relative close proximity to each other and to the ventricular heart chambers compared to the second sensing vector selected at block 304, to provide sensing of a relatively "near-field" ventricular signal for sensing R-waves. The first sensing vector may be a vertical sensing vector (with respect to an upright or standing position of the patient) or approximately aligned with the cardiac axis for maximizing the amplitude of R-waves in the first cardiac electrical signal for reliable R-wave sensing. The first sensing electrode vector, however, is not limited to any particular interelectrode spacing or orientation and may be selected as any available electrode pair.

The second sensing electrode vector used to obtain a second cardiac electrical signal at block 304 may be a relatively long bipole having an inter-electrode distance that is greater than the first sensing electrode vector. For example, the second sensing electrode vector may be selected as the vector between one of the pace sense electrodes 28 or 30 and ICD housing 15, one of defibrillation electrodes 24 or 26 and housing 15 or other combinations of one electrode along the distal portion of the lead 16 and the housing 15. This second sensing vector may be orthogonal or almost orthogonal to the first sensing vector in some examples, but the first and second sensing vectors are not required to be orthogonal vectors. The second sensing electrode vector may receive a relatively more global or far-field cardiac electrical signal compared to the first sensing electrode vector. The second cardiac electrical signal received by the second sensing vector selected at block 304 may be analyzed by control circuit 80 for detecting P-wave oversensing. In other examples, the sensing vector 1 and sensing vector 2 selected for sensing the first and second cardiac electrical signals at blocks 302 and 304 may be the same sensing electrode vector, such that single cardiac electrical signal is received by the sensing circuit 86, but the raw, received signal is processed by two different sensing channels 83 and 85 of sensing circuit 86 having different filtering and/or other signal processing features to sense two different cardiac electrical signals, one used by the first sensing channel 83 for detecting R-waves and one sensed by the second sensing channel for performing signal feature and morphological analysis.

Sensing circuit 86 may produce an R-wave sensed event signal at block 306 in response to the first sensing channel 83 detecting an R-wave sensing threshold crossing by the first cardiac electrical signal. The R-wave sensed event signal may be passed to control circuit 80. In response to the R-wave sensed event signal, down-going "yes" branch of block 306, control circuit 80 is triggered at block 308 to store a segment of the second cardiac electrical signal received from the second sensing channel 85 over a predetermined time interval. Segments of the second cardiac electrical signal may be stored in a circulating buffer of memory 82 configured to store multiple sequential segments, where storage of each segment is triggered by an R-wave sensed event signal produced by the first sensing channel 83. A digitized segment of the second cardiac electrical signal may be 100 to 500 ms long, for example, including sample points before and after the time of the R-wave sensed event signal. The segment of the second cardiac electrical signal may or may not be centered in time on the R-wave sensed event signal received from sensing circuit 86. For instance, the segment may extend 100 ms after the R-wave sensed event signal and be 200 to 500 ms in duration such that the segment extends from about 100 to 400 ms before the R-wave sensed event signal to 100 ms after. In other examples, the segment may be centered on the R-wave sensed event signal or extend a greater number of sample points after the R-wave sensed event signal than before. In one example, the buffered segment of the cardiac electrical signal is at least 50 sample points obtained at a sampling rate of 256 Hz, or about 200 ms. In another example, the buffered segment is at least 92 sample points, or approximately 360 ms, sampled at 256 Hz and is available for analysis for detecting P-wave oversensing.

Memory 82 may be configured to store a predetermined number of second cardiac electrical segments, e.g., at least 1 and in some cases two or more cardiac electrical signal segments, in circulating buffers such that the oldest segment is overwritten by the newest segment. However, previously stored segments may never be analyzed for P-wave oversensing detection and be overwritten if an R-sense confirmation threshold is not reached at block 314 as described below. In some examples, at least one segment of the second cardiac electrical signal may be stored and if not needed for detecting P-wave oversensing, the segment is overwritten by the next segment corresponding to the next R-wave sensed event signal.

In addition to buffering a segment of the second cardiac electrical signal, control circuit 80 responds to the R-wave sensed event signal produced at block 306 by determining an RRI at block 310 ending with the current R-wave sensed event signal and beginning with the most recent preceding R-wave sensed event signal. The timing circuit 90 of control circuit 80 may pass the RRI timing information to the tachyarrhythmia detection circuit 92 which adjusts tachyarrhythmia interval counters at block 312. If the RRI is longer than a tachycardia detection interval (TDI), the tachyarrhythmia interval counters remain unchanged. If the RRI is shorter than the TDI but longer than a fibrillation detection interval (FDI), e.g., if the RRI is in a tachycardia detection interval zone, a VT interval counter is increased at block 312. If the RRI is shorter than or equal to the FDI, a VF interval counter is increased at block 312. In some examples, a combined VT/VF interval counter is increased if the RRI is less than the TDI.

After updating the tachyarrhythmia interval counters at block 312, tachyarrhythmia detector 92 compares the counter values to an R-sense confirmation threshold at block 314 and to VT and VF detection thresholds at block 332. If a VT or VF detection interval counter has reached an R-sense confirmation threshold, "yes" branch of block 314, the second cardiac electrical signal from sensing channel 85 is analyzed to detect P-wave oversensing that may be causing false R-wave sensed event signals to be produced by the first sensing channel 83, resulting in VT and/or VF counters being increased at block 312. The R-sense confirmation threshold may be a VT or VF interval count value that is greater than one or another higher threshold count value. Different R-sense confirmation thresholds may be applied to the VT interval counter and the VF interval counter. For example, the R-sense confirmation threshold may be a count of two on the VT interval counter and a count of three on the VF interval counter. In other examples, the R-sense confirmation threshold is a higher number, for example five or higher, but may be less than the number of VT or VF intervals required to detect VT or VF. In addition or alternatively to applying an R-sense confirmation threshold to the individual VT and VF counters, an R-sense confirmation threshold may be applied to a combined VT/VF interval counter. It is recognized that in some examples, VT detection may not be enabled and VF detection may be enabled. In this case, only a VF interval counter is updated at block 312 in response to RRI determinations and the R-sense confirmation threshold may be applied to the VF interval counter at block 314.

If the R-sense confirmation threshold is not reached by any of the tachyarrhythmia interval counters at block 314, the control circuit 80 waits for the next R-wave sensed event signal at block 308 to buffer the next segment of the second cardiac electrical signal. If the R-sense confirmation threshold is reached at block 314, e.g., when the VF interval counter is greater than 2, the control circuit 80 begins analysis of the second cardiac electrical signal segments for detecting P-wave oversensing.

At block 316, control circuit 80 may retrieve one or more notch filtered signal segments stored in memory 82. In some examples, the stored second cardiac electrical signal segments are notch filtered by control circuit 80 at block 316, e.g., by a firmware implemented notch filter, after the R-sense confirmation threshold is reached. In other examples, the notch-filtered signal is received from the second sensing channel 85 as shown in FIG. 4 and buffered in memory 82 for retrieval by control circuit 80. From each consecutive non-rectified, notch-filtered, second cardiac electrical signal segment buffered in response to an R-wave sensed event signal after the R-sense confirmation threshold is reached, control circuit 80 determines the maximum peak-to-peak amplitude. The maximum peak-to-peak amplitude is determined for at least three consecutively buffered cardiac signal segments to enable determination of two amplitude differences between two consecutive pairs of maximum peak-to-peak amplitudes as described above in conjunction with FIG. 6A. At block 318, control circuit 80 determines the differences between consecutively determined peak-to-peak amplitudes.

Once three consecutively determined peak-to-peak amplitudes are available, so that two consecutive amplitude differences can be determined at block 318, control circuit 80 may apply criteria for detecting an alternating pattern of the peak amplitudes at block 320. The criteria applied at block 320 may correspond to the examples described above in conjunction with FIG. 6A. It is to be understood that, in some cases, when the R-sense confirmation threshold is first reached, the peak-to-peak amplitudes of three consecutively buffered cardiac electrical signal segments may not be available since the determination of the peak-to-peak amplitudes from a buffered segment may not begin until the R-sense confirmation threshold is reached. Two more R-wave sensed event signals and corresponding buffered second cardiac electrical signal segments may be required before the first determination of an alternating pattern can be made at block 320.

As described above, control circuit 80 may detect an alternating pattern of maximum peak-to-peak amplitude by determining the maximum peak-to-peak amplitudes of three consecutive segments, identifying the highest maximum amplitude of two consecutively determined peak-to-peak amplitudes, set a difference threshold as a percentage of the highest maximum peak-to-peak amplitude, then compare the difference in the two consecutively determined maximum peak-to-peak amplitudes to the difference threshold. Two consecutive peak-to-peak amplitude differences are determined from three consecutively determined peak-to-peak amplitudes. The two consecutive differences may be compared to a first set of criteria for detecting a high-low-high pattern as described in conjunction with example 151a of FIG. 6A. If the high-low-high pattern is not detected, the two consecutive differences may be compared to a second set of criteria for detecting a low-high-low pattern as described in conjunction with example 151b of FIG. 6A. In other examples, control circuit 80 may apply the low-high-low amplitude difference criteria first and, if unmet, apply the high-low-high amplitude difference criteria second or apply both low-high-low and high-low-high criteria in parallel for detecting an alternating pattern of the maximum peak-to-peak amplitudes of three consecutive second cardiac electrical signal segments.

When an alternating pattern is not detected at block 320, control circuit 80 may determine if the number of VT and/or VF intervals required to detect VT or VF has been reached at block 332. When a threshold number of intervals to detect (NID) is not reached by the VT interval counter, VF interval counter, or combined VT/VF interval counter, control circuit 80 returns to block 310 to continue determining RRIs and analyzing second cardiac electrical signal segments as long as the R-sense confirmation threshold is satisfied (block 314).

When an alternating pattern is detected at block 320, control circuit 80 identifies which of the three consecutive segments correspond to suspected true sensed R-waves at block 322, based on the alternating pattern identified. For example, when a high-low-high amplitude pattern is identified, the first and third cardiac electrical signal segments are identified as corresponding to suspected true sensed R-waves and the second, middle cardiac electrical signal segment is identified as a suspected oversensed P-wave. When a low-high-low amplitude pattern is detected at block 320, the middle cardiac electrical signal segment is identified as corresponding to a suspected true sensed R-wave, and the first and third cardiac electrical signal segments are identified as suspected P-wave oversensing segments, corresponding to R-wave sensed event signals that are suspected to be false.

At block 326, gross morphology metrics are determined for the cardiac electrical signal segment(s) identified as corresponding to a suspected true sensed R-wave. The gross morphology metrics may be determined by processing and analyzing one or both the rectified, notch-filtered segment of the second cardiac electrical signal and/or the non-rectified, notch-filtered segment as described above in conjunction with FIGS. 7 and 8. Accordingly, the notch-filtered signal segment may be rectified at block 324 (e.g., by the second sensing channel 85 of FIG. 4), and control circuit 80 may use the rectified, notch-filtered signal segment at block 326 for determining the gross morphology metrics. The gross morphology metrics may include an amplitude metric and a signal width metric as described above in conjunction with FIGS. 7 and 8, respectively. When the suspected true R-wave cardiac electrical signal segment(s) of the alternating signal feature pattern are determined to include a tachyarrhythmia morphology at block 328, based on tachyarrhythmia morphology criteria being met, the suspected true R-wave(s) is(are) not verified as true sensed R-waves. In response to detecting at least one tachyarrhythmia morphology at block 328 in the alternating pattern of signal segments, withholding of a VT or VF detection due to suspected PWOS is inhibited by withholding detection of PWOS evidence at block 330 even though an alternating pattern of signal segments may be detected. For example, as described in conjunction with FIGS. 7 and 8, a suspected true sensed R-wave may not be verified when one of the gross morphology amplitude metric or the gross morphology signal width metric is greater than a respective true sensed event threshold value. In this case, a tachyarrhythmia morphology is detected at block 328 and PWOS evidence detection is not made at block 330, even when the alternating pattern of peak-to-peak amplitude is detected at block 320. An oversensing evidence flag may be set to 0 at block 330, or a PWOS counter may be adjusted according to the number of times PWOS evidence has been detected over the last Y R-wave sensed event signals.

When tachyarrhythmia morphology criteria are not met, e.g., when both of the gross morphology amplitude feature and the gross morphology signal width feature are less than the true sensed event threshold, a tachyarrhythmia morphology is not detected at block 328 for the given signal segment. The suspected true R-wave sensed event is verified. In response to the suspected true R-wave sensed event(s) being verified in the alternating pattern of signal features, PWOS evidence is detected at block 334. A PWOS evidence flag may be set to 1 at block 334, or a PWOS counter may be adjusted to increase the number of times PWOS evidence has been detected over the last Y R-wave sensed event signals.

The suspected true R-wave sensed event signal segments are not necessarily determined to be false R-waves when the gross morphology parameters meet tachyarrhythmia morphology criteria at block 328. However, when the tachyarrhythmia morphology criteria are met, e.g., when one or both gross morphology metrics exceed the true sensed event signal threshold, the suspected true sensed R-wave signal segments cannot be verified and may represent true ventricular tachyarrhythmia signal segments. Withholding of a VT or VF detection due to possible PWOS is inhibited in the presence of a relatively high gross morphology amplitude metric and/or relatively high gross morphology signal width metric, both correlated to a tachyarrhythmia morphology. When the gross morphology metrics are relatively low, the suspected R-wave sensed event signals may be true R-waves but relatively low in amplitude, which may lead to frequent PWOS when the R-wave sensing threshold is set based on the maximum peak amplitude of a sensed signal. In this case, a PWOS evidence detection is made at block 334.

Control circuit 80 continues to analyze segments of the second cardiac electrical signal for detecting PWOS evidence (blocks 316-328) as long as the R-sense confirmation threshold is met at block 314. If the VT and VF interval counters no longer meet the R-sense confirmation threshold at block 314, the PWOS evidence counter or buffer may be cleared or reset. The PWOS evidence counter or buffer may begin counting PWOS detections, or setting PWOS evidence buffer flags in a first-in-first-out basis, the next time the R-sense confirmation threshold is reached. When the NID is reached at block 332, based on the values of the VT and/or VF interval counters, control circuit 80 determines whether PWOS is detected at block 336. In order to detect PWOS and cause a VT or VF detection to be withheld, the number of PWOS evidence flags, e.g., stored in a first-in-first out buffer, or value of a PWOS evidence counter, is required to reach a threshold number. For example, if a PWOS event flag is set to "1" for at least eight out of the most recent 32 buffered second cardiac electrical signal segments, PWOS is detected at block 336. The oversensing threshold applied to the PWOS evidence counter or flags may be a fixed threshold or adjustable based on the NID. For example, control circuit 80 may set the oversensing threshold to a relatively lower value when the NID is relatively low and increase the oversensing threshold when the NID is relatively high.

The VT or VF detection is withheld at block 342 and no ventricular tachyarrhythmia therapy is delivered in response to the PWOS detection at block 336. As long as the NID continues to be met, control circuit 80 may continue to update the PWOS evidence counter as new R-waves are sensed to determine if the oversensing threshold is still being met at block 336. In some examples, control circuit 80 may determine if termination criteria are met at block 344 when PWOS detection does not occur. Termination of the fast rhythm may be detected based on a predetermined number of RRIs that are greater than a tachyarrhythmia detection interval or when a mean, median or other metric of RRIs determined over predetermined time interval is greater than a tachyarrhythmia detection interval. For example, when a threshold number of RRIs longer than the VT detection interval (e.g., when VT detection is enabled) or longer than the VF detection interval (e.g., when VT detection is not enabled) are detected subsequent to the NID being met, tachyarrhythmia termination may be detected at block 344. In one example, termination is detected at block 344 when at least eight consecutive long RRIs, e.g., greater than the VT detection interval, are detected. In another example, control circuit 80 may detect termination at block 344 when a predetermined time interval elapses and a median RRI is greater than the VT detection interval. For instance, when the median RRI of the most recent 12 RRIs is always greater than the VT detection interval for at least 20 seconds, or other predetermined time period, control circuit 80 may detect termination at block 344. Control circuit 80 may reset the VT and VF interval counters and return to block 310 in response to detecting termination.

When the NID is met at block 332 and PWOS is not detected at block 336, the VT or VF episode is detected at block 338. Therapy delivery circuit 84 may deliver a VT or VF therapy at block 340 in response to the VT/VF detection. It is to be understood that other criteria may be applied before detecting the VT or VF at block 338. For example, various noise rejection criteria, T-wave oversensing rejection criteria, supraventricular tachycardia (SVT) rejection criteria, etc. may be required to be unmet before detecting VT/VF at block 338.

It should be understood that, depending on the example, certain acts or events of any of the methods described herein can be performed in a different sequence, may be added, merged, or left out altogether (e.g., not all described acts or events are necessary for the practice of the method). Moreover, in certain examples, acts or events may be performed concurrently, e.g., through multi-threaded processing, interrupt processing, or multiple processors, rather than sequentially. In addition, while certain aspects of this disclosure are described as being performed by a single circuit or unit for purposes of clarity, it should be understood that the techniques of this disclosure may be performed by a combination of units or circuits associated with, for example, a medical device.

In one or more examples, the functions described may be implemented in hardware, software, firmware, or any combination thereof. If implemented in software, the functions may be stored as one or more instructions or code on a computer-readable medium and executed by a hardware-based processing unit. Computer-readable media may include computer-readable storage media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPLAs), or other equivalent integrated or discrete logic circuitry. Accordingly, the term "processor," as used herein may refer to any of the foregoing structure or any other structure suitable for implementation of the techniques described herein. Also, the techniques could be fully implemented in one or more circuits or logic elements.

Thus, a medical device has been presented in the foregoing description with reference to specific examples. It is to be understood that various aspects disclosed herein may be combined in different combinations than the specific combinations presented in the accompanying drawings. It is appreciated that various modifications to the referenced examples may be made without departing from the scope of the disclosure and the following claims.

What is claimed is:

1. A medical device comprising:
   a cardiac electrical signal sensing circuit configured to:
   sense at least one cardiac electrical signal;
   detect cardiac events from the at least one cardiac electrical signal;
   a control circuit configured to detect tachyarrhythmia based on the cardiac events detected from the at least one cardiac electrical signal meeting tachyarrhythmia criteria; and
   a therapy delivery circuit configured to generate a therapy in response to the control circuit detecting the tachyarrhythmia;

the control circuit further configured to:
in response to each one of a plurality of cardiac events detected from the at least one cardiac electrical signal, determine a signal feature from a segment of the at least one cardiac electrical signal;
detect an alternating pattern of the signal feature determined from consecutive segments of the at least one cardiac electrical signal;
from each of at least one segment of the consecutive segments of the at least one cardiac electrical signal, determine at least one gross morphology metric by determining one of:
an amplitude metric as the at least one gross morphology metric; or
a maximum signal pulse width metric as the at least one gross morphology metric;
compare the at least one gross morphology metric to tachyarrhythmia morphology criteria;
determine that the at least one gross morphology metric does not meet the tachyarrhythmia morphology criteria;
detect cardiac event oversensing in response to the at least one gross morphology metric not meeting the tachyarrhythmia morphology criteria and detecting the alternating pattern;
withhold a tachyarrhythmia detection in response to detecting the cardiac event oversensing; and
control the therapy delivery circuit to withhold the therapy when the detection of the tachyarrhythmia is withheld.

2. The medical device of claim 1, wherein the control circuit is further configured to:
in response to detecting the alternating pattern, identify at least one segment of the at least one cardiac electrical signal corresponding to a suspected true sensed cardiac event based on the alternating pattern; and
determine the at least one gross morphology metric from the at least one segment corresponding to the suspected true sensed cardiac event.

3. The medical device of claim 1, wherein the control circuit is further configured to:
detect evidence of a tachyarrhythmia morphology in response to the at least one gross morphology metric determined from each of at least one segment of the consecutive segments meeting the tachyarrhythmia morphology criteria; and
withhold the cardiac event oversensing detection in response to detecting the alternating pattern when the at least one gross morphology metric from at least one of the consecutive segments meets the tachyarrhythmia morphology criteria.

4. The medical device of claim 1, wherein the control circuit is configured to detect the alternating pattern of the signal features by:
determining a first signal feature from a first signal segment of the at least one cardiac electrical signal, a second signal feature from a second signal segment of the at least one cardiac electrical signal and a third signal feature from a third signal segment of the at least one cardiac electrical signal, the first, second and third signal segments corresponding to first, second and third cardiac events, respectively, detected consecutively from the at least one cardiac electrical signal;
setting a first difference threshold based on one of the first signal feature or the second signal feature;
determining a first difference between the first signal feature and the second signal feature;
determining that the first difference is greater than the first difference threshold;
setting a second difference threshold based on one of the second signal feature or the third signal feature;
determining a second difference between the second signal feature and the third signal feature;
determining that the second difference is greater than the second difference threshold; and
detecting the alternating pattern in response to the first difference being greater than the first difference threshold and the second difference being greater than the second difference threshold.

5. The medical device of claim 4, wherein the control circuit is configured to determine each of the first signal feature, the second signal feature and the third signal feature by determining a first maximum peak-to-peak amplitude, a second maximum peak-to-peak amplitude, and a third maximum peak-to-peak amplitude from the first, second, and third signal segments, respectively.

6. The medical device of claim 4, wherein the control circuit is further configured to:
determine a third difference between the first signal feature and the third signal feature;
determine that the third difference is less than a stability threshold; and
detect the alternating pattern of the signal features based on the first and second differences being greater than the first and second difference thresholds, respectively, and the third difference being less than the stability threshold.

7. The medical device of claim 1, wherein the control circuit is configured to detect the alternating pattern of the signal features by detecting an alternating pattern of at least one of a peak-to-peak amplitude, a cardiac event interval, or a polarity of a maximum peak amplitude.

8. The medical device of claim 1, wherein the control circuit is configured to determine the at least one gross morphology metric as the amplitude metric by:
determining a maximum amplitude of the segment;
determining a summation of a plurality of sample point amplitudes of the segment; and
dividing the summation by the maximum amplitude.

9. The medical device of claim 1, wherein the control circuit is configured to determine the at least one gross morphology metric as the maximum signal pulse width metric by:
identifying a plurality of signal pulses of the segment;
determining a signal pulse width of each of the plurality of signal pulses; and
determine a maximum signal pulse width out of the determined signal pulse widths.

10. The medical device of claim 1, wherein the control circuit is further configured to:
determine the at least one gross morphology metric by:
determining a first gross morphology metric as the amplitude metric; and
determining a second gross morphology metric as the maximum signal pulse width metric;
determine that the amplitude metric is less than or equal to a first threshold;
determine that the maximum signal pulse width metric is less than or equal to a second threshold; and
determine that the tachyarrhythmia morphology criteria are not met in response to both the amplitude metric being less than or equal to the first threshold and the maximum signal pulse width metric being less than or equal to the second threshold.

11. The medical device of claim 1, wherein the control circuit is further configured to:
  detect evidence of oversensing by detecting an alternating pattern of the signal features during a predetermined number of the consecutive segments;
  determine that the evidence of oversensing has been detected a threshold number of times, wherein the threshold number of times is a proportion of a number of cardiac event intervals between consecutively detected cardiac events from the at least one cardiac electrical signal required to detect the tachyarrhythmia; and
  detect the cardiac event oversensing in response to determining that the evidence of oversensing has been detected the threshold number of times.

12. The medical device of claim 11, wherein the control circuit is configured to adjust the threshold number of times in response to a change in the number of cardiac event intervals required to detect the tachyarrhythmia.

13. The medical device of claim 1, wherein:
  the sensing circuit is configured to:
    sense a first cardiac electrical signal of the at least one cardiac electrical signal via a first sensing electrode vector;
    detect the cardiac events from the first cardiac electrical signal; and
    sense a second cardiac electrical signal of the at least one cardiac electrical signal via a second sensing electrode vector different than the first sensing electrode vector; and
  the control circuit is configured to:
    determine the signal feature from the second cardiac electrical signal; and
    detect the alternating pattern of the signal feature determined from consecutive segments of the second cardiac electrical signal.

14. The medical device of claim 1, wherein the control circuit is configured to not schedule the therapy in response to detecting the cardiac event oversensing.

15. The medical device of claim 1, wherein the control circuit is further configured to:
  determine two consecutive cardiac event intervals between consecutive cardiac events of the plurality of cardiac events;
  determine that a sum of the two consecutive cardiac event intervals falls within a threshold range; and
  determine the signal feature for detecting the alternating pattern from each of the consecutive segments corresponding to each of the consecutive cardiac events of the two consecutive cardiac event intervals.

16. A method comprising:
  sensing at least one cardiac electrical signal;
  detecting cardiac events from the first cardiac electrical signal;
  detecting tachyarrhythmia based on the cardiac events detected from the at least one cardiac electrical signal meeting a tachyarrhythmia criteria;
  generating a therapy in response to detecting tachyarrhythmia;
  the method further comprising:
    in response to each one of a plurality of cardiac events detected from the at least one cardiac electrical signal, determining a signal feature from a segment of the at least one cardiac electrical signal;
    detecting an alternating pattern of the signal feature determined from consecutive segments of the at least one cardiac electrical signal;
    from each of at least one segment of the consecutive segments of the at least one cardiac electrical signal, determining at least one gross morphology metric by determining one of:
      an amplitude metric as the at least one gross morphology metric; or
      a maximum signal pulse width metric as the at least one gross morphology metric;
    compare the at least one gross morphology metric to tachyarrhythmia morphology criteria;
    determining that the at least one gross morphology metric does not meet the tachyarrhythmia morphology criteria;
    detecting cardiac event oversensing in response to the at least one gross morphology metric not meeting the tachyarrhythmia morphology criteria and detecting the alternating pattern;
    withholding a tachyarrhythmia detection in response to detecting the cardiac event oversensing; and
    withholding the therapy when the detection of the tachyarrhythmia is withheld.

17. The method of claim 16, further comprising:
  in response to detecting the alternating pattern, identifying at least one segment of the at least one cardiac electrical signal corresponding to a suspected true sensed cardiac event based on the alternating pattern; and
  determining the at least one gross morphology metric from the at least one segment corresponding to the suspected true sensed cardiac event.

18. The method of claim 16, further comprising:
  detecting evidence of a tachyarrhythmia morphology in response to the at least one gross morphology metric determined from each of at least one segment of the consecutive segments meeting the tachyarrhythmia morphology criteria; and
  withholding detecting the cardiac event oversensing in response to detecting the alternating pattern when the at least one gross morphology metric from at least one of the consecutive segments meets the tachyarrhythmia morphology criteria.

19. The method of claim 16, wherein detecting the alternating pattern of the signal features comprises:
  determining a first signal feature from a first signal segment of the at least one cardiac electrical signal, a second signal feature from a second signal segment of the at least one cardiac electrical signal and a third signal feature from a third signal segment of the at least one cardiac electrical signal, the first, second and third signal segments corresponding to first, second and third cardiac events, respectively, detected consecutively from the at least one cardiac electrical signal;
  setting a first difference threshold based on a percentage of one of the first signal feature or the second signal feature;
  determining a first difference between the first signal feature and the second signal feature;
  comparing the first difference to the first difference threshold;
  setting a second difference threshold based on one of the second signal feature or the third signal feature;
  determining a second difference between the second signal feature and the third signal feature;
  comparing the second difference to the second difference threshold; and
  detecting the alternating pattern in response to the first difference being greater than the first difference threshold and the second difference being greater than the second difference threshold.

20. The method of claim 19, further comprising:
determining a third difference between the first signal feature and the third signal feature;
determining that the third difference is less than a stability threshold; and
detecting the alternating pattern based on the first and second differences being greater than the first and second difference thresholds, respectively, and the third difference being less than the stability threshold.

21. The method of claim 16, wherein detecting the alternating pattern of the signal features comprises detecting an alternating pattern of at least one of a peak-to-peak amplitude, a cardiac event interval, or a polarity of a maximum peak amplitude.

22. The method of claim 16, wherein determining the at least one gross morphology metric comprises one of:
determining the gross morphology metric as the amplitude metric by:
(a) determining a maximum amplitude of the segment; determining a summation of a plurality of sample point amplitudes of the segment; and
dividing the summation by the maximum amplitude; or
determining the gross morphology metric as the maximum signal pulse width metric by:
(b) identifying a plurality of signal pulses of the segment;
determining a signal pulse width of each of the plurality of signal pulses; and
determining a maximum signal pulse width out of the determined signal pulse widths.

23. The method of claim 16, further comprising:
determining the at least one gross morphology metric by:
determining a first gross morphology metric by determining the amplitude metric;
determining a second gross morphology metric by determining the maximum signal pulse width metric;
determining that the amplitude metric is less than or equal to a first threshold;
determining that the maximum signal pulse width metric is less than or equal to a second threshold; and
determining that the tachyarrhythmia morphology criteria are not met in response to both the amplitude metric being less than or equal to the first threshold and the maximum signal pulse width metric being less than or equal to the second threshold.

24. The method of claim 16, further comprising:
detecting evidence of oversensing by detecting an alternating pattern of the signal features during a predetermined number of consecutive segments;
determining that the evidence of oversensing has been detected a threshold number of times, wherein the threshold number of times is a proportion of a number of cardiac event intervals between consecutively detected cardiac events from the at least one cardiac electrical signal required to detect the tachyarrhythmia; and
detecting the cardiac event oversensing in response to determining that the evidence of oversensing has been detected the threshold number of times.

25. The method of claim 24, further comprising adjusting the threshold number of times in response to a change in the number of cardiac event intervals required to detect the tachyarrhythmia.

26. The method of claim 16, further comprising:
sensing a first cardiac electrical signal of the at least one cardiac electrical signal via a first sensing electrode vector;
detecting the cardiac events from the first cardiac electrical signal;
sensing a second cardiac electrical signal of the at least one cardiac electrical signal via a second sensing electrode vector different than the first sensing electrode vector;
determining the signal feature from the second cardiac electrical signal; and
detecting the alternating pattern of the signal feature determined from consecutive segments of the second cardiac electrical signal.

27. The method of claim 16, further comprising not scheduling the therapy in response to detecting the cardiac event oversensing.

28. The method of claim 16, further comprising:
determining two consecutive cardiac event intervals between consecutive cardiac events of the plurality of cardiac events;
determining that a sum of the two consecutive cardiac event intervals falls within a threshold range; and
determining the signal feature for detecting the alternating pattern from each of the consecutive segments corresponding to each of the consecutive cardiac events of the two consecutive cardiac event intervals.

29. A non-transitory computer-readable medium storing a set of instructions which, when executed by a control circuit of a medical device, cause the medical device to:
sense at least one cardiac electrical signal;
detect cardiac events from the at least one cardiac electrical signal;
detect tachyarrhythmia based on the cardiac events detected from the at least one cardiac electrical signal meeting a tachyarrhythmia criteria; and
generate a therapy in response to detecting tachyarrhythmia;
the instructions further causing the medical device to:
in response to each one of a plurality of cardiac events detected from the at least one cardiac electrical signal, determine a signal feature from a segment of the at least one cardiac electrical signal;
detect an alternating pattern of the signal feature determined from consecutive segments of the second cardiac electrical signal;
from each of at least one segment of the consecutive segments of the at least one cardiac electrical signal, determine at least one gross morphology metric by determining one of:
an amplitude metric as the at least one gross morphology metric; or
a maximum signal pulse width metric as the at least one gross morphology metric;
compare the at least one gross morphology metric to tachyarrhythmia morphology criteria;
determine that the at least one gross morphology metric does not meet the tachyarrhythmia morphology criteria;
detect cardiac event oversensing in response to the at least one gross morphology metric not meeting the tachyarrhythmia morphology criteria and detecting the alternating pattern;
withhold a tachyarrhythmia detection in response to detecting the cardiac event oversensing; and withhold the therapy when the detection of the tachyarrhythmia is withheld.

\* \* \* \* \*